United States Patent
Swinger et al.

(10) Patent No.: US 6,325,792 B1
(45) Date of Patent: Dec. 4, 2001

(54) OPHTHALMIC SURGICAL LASER AND METHOD

(76) Inventors: Casimir A. Swinger, 9 W. 67th St., New York, NY (US) 10023; Shui T. Lai, 1223 Orchard Glen Cir., Encinitas, CA (US) 92024

(*) Notice: Subject to any disclaimer, the term of this patent is extended or adjusted under 35 U.S.C. 154(b) by 0 days.

(21) Appl. No.: 08/287,000

(22) Filed: Aug. 8, 1994

Related U.S. Application Data

(63) Continuation-in-part of application No. 08/051,033, filed on Apr. 20, 1993, which is a continuation-in-part of application No. 07/968,060, filed on Oct. 26, 1992, now abandoned, which is a continuation-in-part of application No. 07/788,424, filed on Nov. 6, 1991, now abandoned.

(51) Int. Cl.$^7$ .................................................... A61B 17/36
(52) U.S. Cl. .................................................... 606/4; 606/11
(58) Field of Search .................................... 606/2, 3, 4, 5, 606/6, 10, 11, 12; 128/898

(56) References Cited

U.S. PATENT DOCUMENTS

| | | | | |
|---|---|---|---|---|
| 3,629,602 | * | 12/1971 | Fierster | 359/330 |
| 4,313,416 | * | 2/1982 | Nimigata | 606/9 |
| 4,464,761 | * | 8/1984 | Alfono et al. | 372/41 |
| 4,538,608 | * | 8/1985 | L'Esperance | 606/5 |
| 4,648,400 | * | 3/1987 | Schneider et al. | 606/3 |
| 4,648,892 | * | 3/1987 | Kittrelly | 606/7 |
| 4,665,913 | * | 5/1987 | L'Esperance, Jr. | 606/3 |
| 4,707,586 | * | 11/1987 | Bille et al. | 128/395 |
| 4,791,927 | * | 12/1988 | Menger | 606/10 |
| 4,887,592 | * | 12/1989 | Loertscher | 606/5 |
| 4,907,586 | * | 3/1990 | Bille et al. | 606/5 |
| 4,911,711 | * | 3/1990 | Telfair et al. | 606/5 |
| 4,913,142 | | 4/1990 | Kittrell et al. | |
| 4,941,093 | * | 7/1990 | Marshall et al. | 606/5 |
| 5,163,734 | * | 11/1992 | Munnerlyn | 606/5 |
| 5,188,631 | * | 2/1993 | L'Esperance, Jr. | 606/5 |
| 5,207,668 | * | 5/1993 | L'Esperance, Jr. | 606/5 |

FOREIGN PATENT DOCUMENTS

| | | | | |
|---|---|---|---|---|
| 3532464 | * | 3/1986 | (DE) | 606/4 |
| 296982 | * | 12/1988 | (EP) | 606/5 |
| 8707165 | * | 12/1987 | (WO) | 606/4 |
| 8700748 | * | 2/1987 | (WO) | 606/5 |
| 9111158 | * | 8/1991 | (WO) | 606/5 |

* cited by examiner

Primary Examiner—Angela D. Sykes
Assistant Examiner—Sonya Hans-Oguyen
(74) Attorney, Agent, or Firm—Nolte, Nolte and Hunter, P.C.

(57) ABSTRACT

Low energy, ultra-short (femtosecond) pulsed laser radiation is applied to the patient's eye in one of a number of patterns such that the exposed ocular tissue is ablated or excised through the process of optical breakdown or photodisruption in a very controlled fashion. The process can be gentle enough that the invention makes possible the performance of a number of surgical procedures that in the past could not have been performed at all, such as capsulorhexis, or were performed in a fashion that provided less than an ideal result or excessive trauma to the ocular tissue. Such latter applications include the making of incisions for corneal transplantation, radial and arcuate keratotomy, and intrastromal cavitation. Using the laser inside the eye allows the surgeon to perform glaucoma operations such as trabeculoplasty and iridotomy, cataract techniques such as capsulectomy, capsulorhexis and phacoablation, and vitreo-retinal surgery, such as membrane resection. The various procedures are accomplished by controlling energy flux or irradiance, geometric deposition of beam exposure and exposure time.

14 Claims, 27 Drawing Sheets

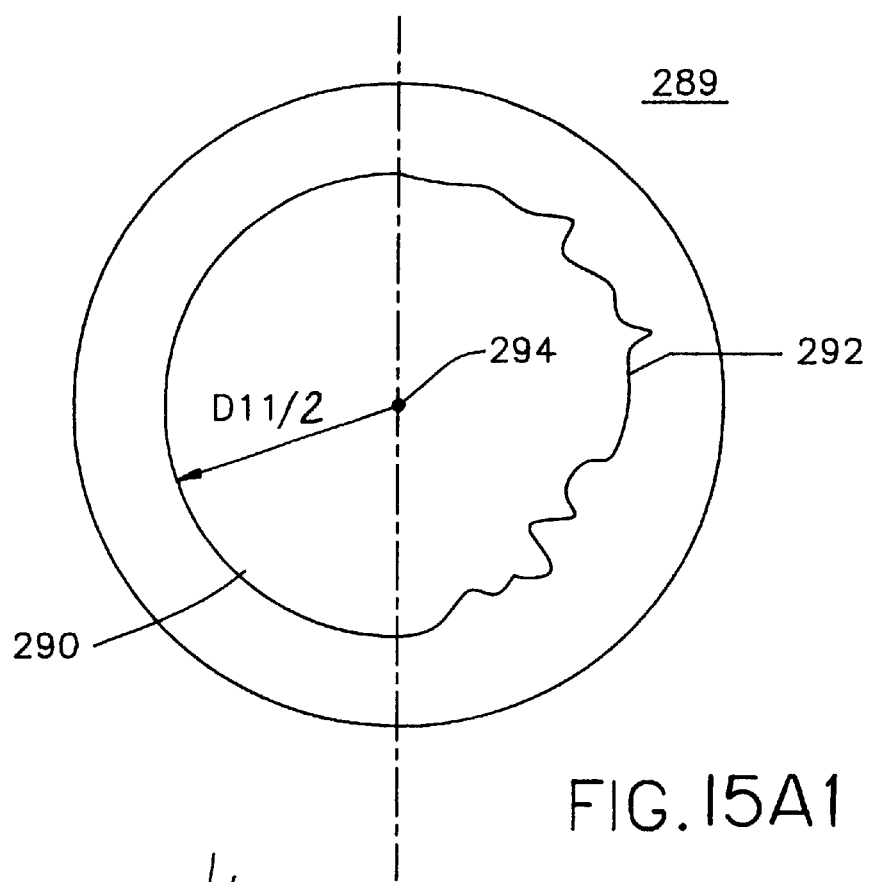
FIG.15A1
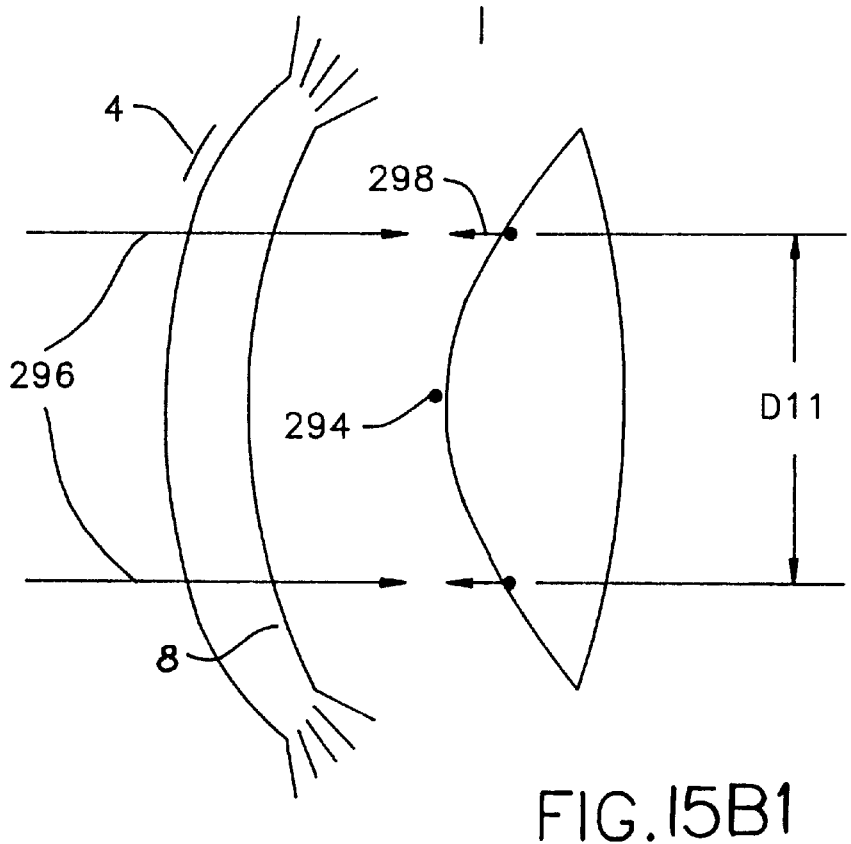
FIG.15B1

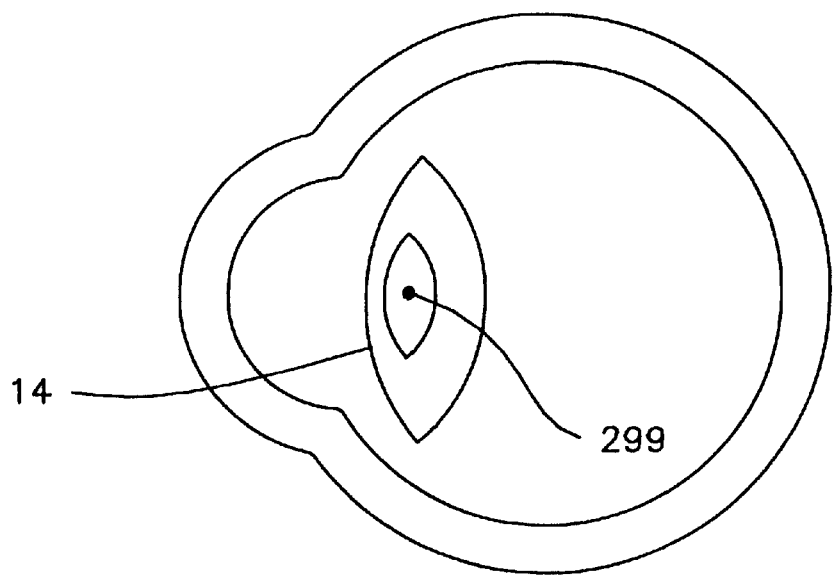
FIG. 15C1
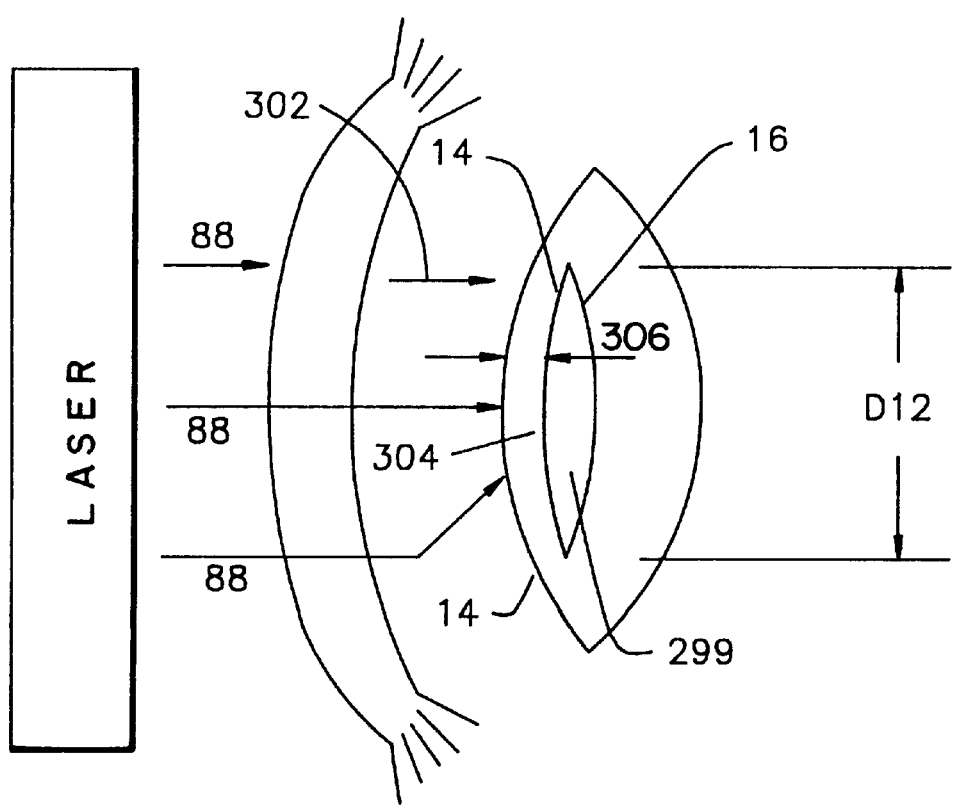
FIG. 15D1

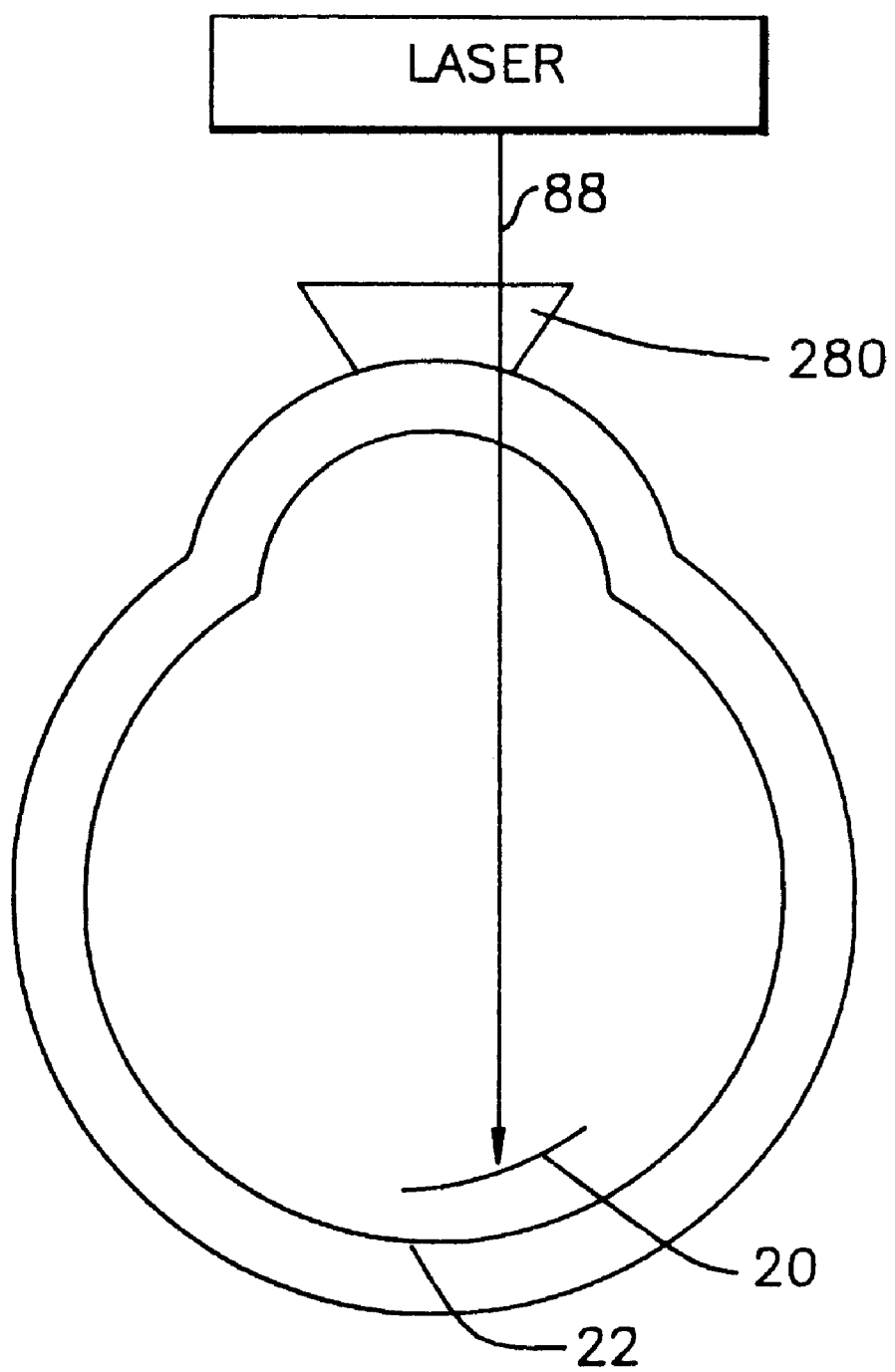
FIG. 15E1

OPHTHALMIC SURGICAL LASER AND METHOD

This is a continuation-in-part of application Ser. No. 07/968,060 filed Oct. 26, 1992 abandoned, claiming priority from that application and any of its parent applications, including Ser. No. 07/788,424 filed Nov. 6, 1991 abandoned by Shui T. Lai, of which the '060 application is a CIP.

This is also a Continuation-in-Part of Ser. No. 08/051,033, pending filed Apr. 20, 1993 by Shui T. Lai., and any of its parent applications.

BACKGROUND OF THE INVENTION

1. Field of the Invention

This invention relates to methods of, and apparatus for, eye surgery, and more particularly to a laser-method and apparatus for corneal and intraocular surgery.

2. Related Art

The concept of correcting refractive errors by changing the curvature of the eye was initially implemented by mechanical methods. These mechanical procedures involve removal of a thin layer of tissue from the cornea by a microkeratome, freezing the tissue at the temperature of liquid $Co_2$, and re-shaping the tissue in a specially designed lathe. The thin layer of tissue is then re-attached to the eye by suture. The drawback of these methods is the lack of reproducibility and hence a poor predictability of surgical results.

With the advent of lasers, various methods for the correction of refractive errors and for general eye surgery have been attempted, making use of the coherent radiation properties of lasers and the precision of the laser-tissue interaction. A $CO_2$ laser was one of the first to be applied in this field. Peyman, et al., in Ophthalmic Surgery, vol. 11, pp. 325–9, 1980, reported laser burns of various intensity, location, and pattern were produced on rabbit corneas. Recently, Horn, et al., in the Journal of Cataract Refractive Surgery, vol. 16, pp. 611–6, 1990, reported that a curvature change in rabbit corneas had been achieved with a $Co:MgF_2$ laser by applying specific treatment patterns and laser parameters. The ability to produce burns on the cornea by either a $CO_2$ or a $Co:MgF_2$ laser relies on the absorption in the tissue of the thermal energy emitted by the laser. Histologic studies of the tissue adjacent to burn sites caused by a $CO_2$ laser reveal extensive damage characterized by a denaturized zone 5–10 $\mu$m deep and a disorganized tissue region extending 50 $\mu$m deep. Such lasers are thus ill suited for eye surgery.

In U.S. Pat. No. 4,784,135 Blum et al. discloses the use of far-ultraviolet excimer laser radiation of wavelengths less than 200 nm to selectively remove biological materials. The removal process is claimed to be by photoetching without using heat as the etching mechanism. Medical and dental applications for the removal of damaged or unhealthy tissue from bone, removal of skin lesions, and the treatment of decayed teeth are cited. No specific use for eye surgery is suggested, and the indicated etch depth of 150 $\mu$m is too great for most eye surgery purposes.

In U.S. Pat. No. 4,718,418, L'Esperance, Jr. discloses the use of a scanning ultraviolet laser to achieve controlled ablative photodecomposition of one or more selected regions of a cornea. According to the disclosure, the laser beam from an excimer laser is reduced in its cross-sectional area, through a combination of optical elements, to a 0.5 mm by 0.5 mm rounded-square beam spot that is scanned over a target by deflectable mirrors. To ablate a corneal tissue surface with such an arrangement, each laser pulse would etch out a square patch of tissue. An etch depth of 14 $\mu$m per pulse is taught for the illustrated embodiment. This etch depth would be expected to result in an unacceptable level of eye damage.

Another technique for tissue ablation of the cornea is disclosed in U.S. Pat. No. 4,907,586 to Bille et al. By focusing a laser beam into a small volume of about 25–30 $\mu$m in diameter, the peak beam intensity at the laser focal point could reach about $10^{12}$ W/cm$^2$. At such a peak power level, tissue molecules are "pulled" apart under the strong electric field of the laser light, which causes dielectric breakdown of the material. The conditions of dielectric breakdown and its applications in ophthalmic surgery had been described in the book "YAG Laser Ophthalmic Microsurgery" by Trokel. Transmissive wavelengths near 1.06 $\mu$m and a frequency-doubled laser wavelength near 530 nm are typically used for the described method. Near the threshold of the dielectric breakdown, the laser beam energy absorption characteristics of the tissue changes from highly transparent to strongly absorbent. The reaction is very violent, and the effects are widely variable. The amount of tissue removed is a highly non-linear function of the incident beam power. Hence, the tissue removal rate is difficult to control. Additionally, accidental exposure of the endothelium to the laser beam is a constant concern. This method is not optimal for corneal surface or intraocular ablation.

An important issue that is largely overlooked in all the above-cited references is the fact that the eye is a living organ. Like most other organs, eye tissue reacts to trauma, whether it is inflicted by a knife or a laser beam. Clinical results have shown that a certain degree of haziness develops in most eyes after laser refractive surgery with the systems taught in the prior art. The principal cause of such haziness is believed to be roughness resulting from cavities, grooves, and ridges formed while laser etching. Additionally, clinical studies have indicated that the extent of the haze also depends in part on the depth of the tissue damage, which is characterized by an outer denatured layer around which is a more extended region of disorganized tissue fibers. Another drawback due to a rough corneal surface is related to the healing process after the surgery: clinical studies have confirmed that the degree of haze developed in the cornea correlates with the roughness of the stromal surface.

The prior art also fails to recognize the benefits of ablating eye tissue with a laser beam having a low energy density. A gentle laser beam, one that is capable of operating at a lower energy density for a surgical procedure, will clearly have the advantage of inflicting less trauma to the underlying tissue. The importance of this point can be illustrated by considering the dynamics of the ablation process on a microscopic scale: the ablation process is basically an explosive event. During ablation, organic materials are broken into their smaller sub-units, which cumulate a large amount of kinetic energy and are ejected away from the laser interaction point at a supersonic velocity. The tissue around the ablated region absorbs the recoil forces from such ejections. The tissue is further damaged by acoustic shock from the expansion of the superheated plasma generated at the laser interaction point. Accordingly a shallower etch depth or smaller etch volumes involves less ejected mass and acoustic shock, and hence reduces trauma to the eye.

It is therefore desirable to have a method and apparatus for performing eye surgery that overcomes the limitations of the prior art. In particular, it is desirable to provide an improved method of eye surgery which has accurate control of tissue removal, flexibility of ablating tissue at any desired location with predetermined ablation depth or volume, an optically smooth finished surface after the surgery, and a gentle surgical beam for laser ablation action. The present invention provides such a method and apparatus.

In many cases, the procedures proposed have been performed in the past, but they have been accompanied by inaccuracy, trauma or ocular damage. In others, they have never been capable of performance because of surgical or technical considerations.

U.S. Pat. No. 4,309,998, Aron nee Rosa et al., issued Jan. 12, 1982, described the process of optical breakdown and photodisruption, whereby tissues, transparent or not, to a given wavelength of laser radiation can be excised or ablated by sharply focusing the beam at a specific point in the tissue while achieving a local power density at the site above the threshold (greater than $10^{12}$ Watts/cm$^2$) for optical breakdown, a complex process involving ionization, plasma formation, and mechanical disruption by secondarily propagated waves. In this patent, the inventors used a YAG laser, emitting at 1064 nm, with pulse widths in the range of 20–400 ps and energies in the range of 2–5 mJ to ablate opacities from the lens of the eye open posterior lens capsules, and cut vitreous membranes.

In their publication "Ophthalmic Neodymium YAG Lasers", Keates et al. describe the basic principles underlying photodisruption with lasers. The definition of power density is given as the ratio of beam energy in Joules divided by pulse length in second times focal spot area in square centimeters. Thus, the shorter the pulse length or the smaller the spot, the greater the power density, which is the determinant in achieving optical breakdown, whose threshold is given as $10^{12}$ W/cm$^2$. Also, it is described that high pulse power and low pulse energy are preferred for cutting or perforating tissue, and that low pulse power and high pulse energy are associated with thermal and biophysical damage mechanisms. By using shorter pulses, an appropriate power density can be achieved in any tissue with a lower energy level, which reduces shock waves and adjacent tissue damage.

U.S. Pat. No. 4,907,586, Bille and Brown, issued Mar. 13, 1990, describes the use of the photodisruptive process for corneal and other eye surgery. In this patent, a quasi-continuous picosecond pulse width laser is used to create optical breakdown in various tissues. The inventors describe, in general, the categories of procedures that may be attempted with such a laser.

One of us (Shui T. Lai) has described technology for producing laser pulses in the femptosecond range, which, as based on the above discussion, allows high power densities to be achieved at much lower energy levels than any described in the art. Experimentally, we ablated tissue by photodisruption at various pulse widths and energy levels and have demonstrated the attainment of superior results with respect to the procedures described herein when operating in the femptosecond range as opposed to the picosecond range, with respect to pulse width. Light and electron microscopy have clearly demonstrated less adjacent damage, sharper incisions, and the ability to more accurately localize the surgical interaction, which is mandatory for optical success.

Corneal operations are typically performed for either therapeutic or optical considerations. In the therapeutic class are such procedures as lamellar keratoplasty and penetrating keratoplasty or corneal transplantation. The classic operation of lamellar keratoplasty is designed to remove scarred, irregular or opaque corneal tissue from across the visually critical central optic zone of the cornea and replacement with a partial donor cornea to restore the corneal shape and clarity, thereby improving vision. It relates also to other operations on the anterior cornea designed primarily to produce changes in the optical imaging of the cornea, thereby correcting optic errors of the eye, such as myopia (nearsightedness), hyperopia (farsightedness), astigmatism, optical aberrations and combinations thereof.

The operation of partial thickness lamellar keratoplasty to remove corneal opacities has been practices for many years (see Brightbill, F S, Corneal Surgery, Chapter 33, C. V. Mosby Co., St. Louis, 1986). It has classically been performed by direct mechanical removal of a circular disc of tissue of constant thickness and replacement thereof with a similarly shaped piece of donor corneal tissue. The optical quality of the final cornea has frequently been known to be irregular or with some interface opacity, and often resulted in reduction of vision from normal. More recently, this procedure has been performed with a high-speed mechanical microkeratome to effect detachment of the anterior disk both from the patient's cornea and from the donor's cornea. However, this technique is technically difficult and accompanied by incomplete or irregular resections, resections of inappropriate depth, and can cause penetration into the eye.

In penetrating keratoplasty, a partial diameter but full-thickness section of the patient's cornea is removed and replaced with a donor corneal button similar in size. Typically, the walls of the incision are vertical, or parallel to the visual axis. This provides a button whose walls are a portion of a cylinder. Also, the transplant button is typically round, as this facilitates use of mechanical trephines. However, many surgeons believe that round buttons may not be ideal for several reasons, involving healing, rejection, and endothelial cell population transplanted. However, there is no technique at present to allow for cutting corneal buttons of any shape, with accuracy. Also, some surgeons believe that walls other than vertical may decrease various complications, such as wound leak, astigmatism, etc. This is not accomplishable by any means.

This operation is notoriously accompanied by high astigmatism following the surgery, which limits its success, and which is believed to result from the healing process of irregularly cut wound margins. Typically, some trephine blade is used to make most of the incision, which is then completed manually with scissors. Surgeons have long sought an ideal way to cut corneal tissue as evidenced by the number of different trephines developed.

Corneal surgery is also performed frequently for modifying the optical or refractive power of the eye. Such operations fall into different categories or approaches. They include the lamellar techniques, whereby corneal tissue is removed from within the cornea, leaving its anterior outermost structure intact, incisional techniques, whereby cuts are made through the anterior surface and to deep in the cornea, thereby causing secondary compensatory changes in the curvature of the anterior cornea, and, most recently, direct ablation or removal of the anterior cornea in a controlled fashion, using an ultraviolet laser, to produce a new surface with different curvature.

Barraquer teaches the general art of altering the anterior corneal curvature of the eye to effect changes in refraction, or optical imaging of the eye, with the operation of keratomileusis, a form of lamellar kerotoplasty. (See IBID, Chpt. 37). In this procedure, a circular lamellar disc of constant thickness centered on the visual axis is removed from the front of the patient's cornea with a high-speed mechanical microkeratome. Following said removal, called a lamellar keratectomy, the resected lamellar disc of constant thickness is placed onto one of two available devices (Barraquer cryolathe, BKS device) to effect modification in shape to produce a lenticule with refractive optical power. Although operationally different, both devices effect the production of a refractive corneal lenticule. The lenticule is produced by volumetric mechanical removal of stromal tissue from the cut and exposed corneal stromal surface of the resected lamellar disc. Such tissue removal may be greatest in the center of the disc, which allows for correction of myopia, or toward the outer periphery, which allows for correction of hyperopia. In any event, the tissue removal is usually such that there is a smooth and regular transition of thickness as one traverses the optically modified (optic zone) area. Following tissue removal from the disc (now called a lenticule), it is replaced onto the patient's cut stromal surface remaining behind after the initial keratectomy. Said replacement results in a new anterior corneal curvature and alteration in the optic imaging of light by the cornea.

In addition, the mechanical microkeratome has also been used in two recently developed lamellar refractive procedures—in-situ keratomileusis and hyperopic lamellar keratectomy. In in-situ keratomileusis, the microkeratome is used to detach a thin slice of constant thickness from the patient's cornea. This is followed by a second keratectomy with the microkeratome, smaller in diameter than the first and concentric within the confines of the first. The initially resected disc is then replaced atop the bed. The second keratectomy also resects a disc of parallel faces or constant thickness. When the cap is replaced, it drops into the cavity, thereby causing flattening of the anterior cornea. The degree of flattening and optical correction is related to the depth and diameter of the second resection. This procedure is to be distinguished from classic keratomileusis performed with a laser for making the second, or optical, ablation, as the physical process is different and in-situ keratomileusis provides a larger functional optical zone, greater refractive correction and greater stability.

In hyperopic lamellar keratectomy a lamellar disc of corneal tissue is deeply removed and simply replaced to effect a correction of hyperopia. The amount of correction is related to the diameter of the resected disc. However, experience has shown that the mechanical microkeratome has the potential of becoming stuck in its passage across the eye, of producing a surface of irregular or poor quality and of being inaccurate with respect to diameter and thickness, all of which compromise the result obtained. Also, there is technical difficulty in using the microkeratome, despite its being automated recently.

Another category of corneal procedures consists of incisional techniques. Here, as in radial keratotomy, for example, the surgeon makes a series of incisions deep into the cornea, sparing a central incision free zone. This results in flattening of the cornea and correction of myopia. Or, various other geometric patterns of incisions may be made, such as transverse or arcuate. These are typically used to correct astigmatism. The major limitation with these techniques is the inability of the surgeon to cut precisely in the desired location and in a reproducible fashion, especially with respect to the length, depth and perpendicularity of the incisions. This results in a lack of reproducibility and inaccuracy. It is well established that incisions too short lead to undercorrection, too long to overcorrection and bothersome visual symptoms, and deviation from perpendicularity, or oblique incisions, like shallow incisions, to undercorrection and instability. Thus, the inability to incise corneal tissue in a reproducible manner, according to plan, has been a major drawback.

A characteristic of the foregoing discussion of operative procedures is that they all attempt to spare the anterior central corneal structure from surgical damage. This is in contrast to the recently developed excimer laser surgical procedure where the anterior surface is progressively ablated and destroyed by the surgery. U.S. Pat. No. 4,732,148, L'Esperance, issued Mar. 22, 1988, discloses a method of applying ultraviolet radiation to the anterior cornea (photorefractive keratectomy) in order to correct the optical errors of myopia, hyperopia, and astigmatism. Unfortunately, the delicate anterior membrane complex of the patient's cornea (primarily Bowman's membrane) is destroyed in the process of removal, leaving a cornea which is anatomically, and perhaps physiologically, abnormal. In addition, two other drawbacks of this method have been noted. The first is the production of haze within the operated cornea, which can be permanent, and which may be associated with visual symptoms or reduction in vision. Haze has been attributed to acoustic shock waves, induced by the laser beam of high energy, propagated in the cornea. Second, the anatomically abnormal cornea develops a healing response such that the outermost epithelial layer, regenerated over the operated area from peripheral unoperated epithelium, frequently demonstrates hyperplasia or thickening postoperatively. This can cause gross inaccuracy or instability of the obtained optical result. Also, pain and delayed rehabilitation along with the long-term use of medications that may cause glaucoma are needed. For this reason, surgeons seek procedures capable of correcting optical errors of the eye while sparing the anterior central cornea.

U.S. Pat. No. 4,903,695, Warner et al., issued Feb. 27, 1990, disclosed a method of performing Barraquer's classic keratomileusis operation using an ultraviolet or infrared laser to effect the tissue modification step, thereby replacing the cryolathe and BKS device. It also circumvents laser damage to the anterior cornea. However, the method requires the use of a mechanical microkeratome to first detach a circular disc of tissue from the patient's cornea, which has limitations as previously described. Following this mechanical cut, the laser irradiation is applied selectively to the cut stromal surface left behind on the patient to remove tissue in a controlled fashion such that when the initially resected disc is replaced onto the bed from which it was removed, a new curvature is imposed onto the anterior corneal surface. In this teaching, the "predetermined curvature" imposed on the ablated corneal bed is intimately related to the final desired anterior curvature of the cornea, and is in fact equal to the final radius of curvature desired minus the thickness of the disc resected by the microkeratome. It is important to note that radiation is applied to resect from the bed, as clearly described in the drawings, a lens of optical power from the cornea, not to create a trough of constant depth, as is the basis of in-situ keratomileusis, which induces a curvature change by a different physical process.

The corneal techniques described above have met with several shortcomings, as partly described. These consist in the inability to precisely and reproducibly cut living corneal tissue with a minimum of trauma to the cornea. The mechanical and manual techniques best exemplify this limitation. When cutting is performed with lasers, the results thus far using existing technology have not demonstrated the ability to cut with minimal trauma and maximal control. One observes a tissue interaction zone which is too large for precise tissue removal, no cutting at all if the power density is below the threshold, or adjacent tissue damage from the energy levels used.

Lasers have been used in glaucoma surgery for years. There are two major classes of glaucoma, open angle and closed angle. In open angle glaucoma, there is difficulty in the eye's intraocular fluid exiting from the eye, thus raising the pressure within the eye, causing glaucoma. The basic problem is the outflow channel for fluid, which does not function well. For this reason, a number of operations have been developed to provide increased outflow. In closed angle glaucoma, the problem lies more in the internal structure of the eye, where various abnormalities allow the pressure to build up behind the iris of the eye, causing a displacement, which in turn compresses or occludes the outflow channel, which is more or less normal. Thus, operations to correct open angle glaucoma are geared to providing outflow from the eye, whereas closed angle glaucoma is corrected by making a full-thickness hole through the iris to allow the free movement of fluid from the back of the eye, where it is made, to the front of the eye, from where it exits the eye.

Typically, two surgical approaches have been utilized. The oldest and most common is utilizing a laser such as an argon laser to achieve the desired effects in trabeculoplasty and iridotomy by photocoagulation, or the vaporization of tissue. In filtration procedures such as trabeculoplasty, minor restructuring of the tissue with partial or complete penetration is accomplished by thermal effects of the laser, thereby causing a change in structure of the trabecular meshwork, which is part of the outflow system of the eye. Surgery alters the structure such that the intraocular fluid can escape from the eye more easily, thereby reducing the eye's pressure in glaucoma patients. Also, the operation of sclerostomy is similarly performed, either from within or without the eye, to create a drainage channel for the intraocular fluid. Also, the operation of trabeculectomy is another modification, whereby a partial thickness flap of the eye's wall, the sclera, is opened, a drainage opening made into the eye itself, and the flap replaced as a partial thickness protector for the interior of the eye. Recently, lasers such as the holmium, an infrared laser, have been used in attempts to provide some of these perforations.

In closed angle glaucoma, an iridotomy, or total penetration through the iris is desired. In addition to using photocoagulation or photovaporization, one can also use photodisruption. The disadvantages of all these techniques are ocular trauma, especially in photodisruption, where each laser pulse produces a significant shock wave that can damage the delicate intraocular structures.

Lasers have also been used in cataract surgery for some time. This includes both for excising the posterior lens capsule, when opacified, and for delivering energy to the lens itself for ablating its interior substance, both to create an opening at the visual axis or to shorten the time of secondary phacoemulsification surgery by first liquefying the interior lens substance, which uses ultrasonic energy to remove the lens material and which is traumatic to the posterior lens capsule and intraocular structures. It is felt that by first ablating the lens (phacoablation) that the time needed for the ultrasound will be reduced. Unfortunately, the lasers proposed thus far, Nd:YAG and Nd:YLF have a considerable acoustic shock component in themselves at the energy levels used. When used to open the posterior capsule of the lens to remove an opacity, shock waves from the currently used Nd:YAG lasers have been shown to be able to cause complications in the posterior eye. Cataract surgery, as presently performed, requires the opening of the anterior capsule of the lens to allow the surgeon access to the lens itself. Currently, no laser has the control and gentleness of beam that allows a smooth and regular opening, or capsulorhexis. To date, this opening has been created manually, with a needle, and this can result in complications if torn irregularly or inappropriately.

Behind the lens, or in the posterior segment of the eye, lies the vitreous humour and retina. Currently, lasers utilizing photodisruption can be used to cut or ablate membranes within the vitreous cavity, but only with significant shock and only at a safe distance from the retina. Surgeons seek a fine cutting laser with minimal shock wave that can allow membranes close to the retina to be resected.

Also, many patients have retinal pathology, such as subretinal membranes or blood vessels. In most instances, these conditions are not treatable as they would cause substantial damage to vision, as the functional part of the retina overlies the abnormal pathology, and attempts to remove or ablate the pathology lead to destruction of the overlying retina. A laser capable of ablating behind the retina with minimal thermal or shock component would allow many patients a surgical option for cure of their blindness.

SUMMARY OF THE INVENTION

The present invention recognizes that an optically smooth corneal surface and a clear intraocular light path (including postoperative clarity) are all critical to successful ophthalmic surgery. The effects of eye surgery on all of the intraocular elements encountered by light traversing the optical path from the cornea to the retina must be considered. The invention was developed with a particular view to preserving these characteristics.

The preferred method of performing a surface ablation of cornea tissue or other organic materials uses a laser source which has the characteristics of providing a shallow ablation depth or region (about 0.2 $\mu$m to about 5.0 $\mu$m), a low ablation energy density threshold (about 0.2 to 5 $\mu$J/(10 $\mu$m)$^2$) and extremely short laser pulses (having a duration of about 10 femtoseconds to about 2 picoseconds per pulse) to achieve precise control of tissue removal. The laser beam cross-sectional area is preferably about 10 $\mu$m in diameter.

The preferred laser system includes a broad gain bandwidth laser, using lasing ions such as titanium, chromium or neodymium (for example, $Ti_3:Al_2O_3$, $Cr:LiSrAlF_6$, Nd:YLF, or similar lasers), with a preferred wavelength of about 400 nm to about 1900 nm, which is generally transmissive in eye tissue.

Each laser pulse is directed to its intended location in or on the eye through a laser beam control means, such as type described in a co-pending, commonly-owned patent application for an invention entitled "Method of, and Apparatus for, Surgery of the Cornea" (U.S. patent application Ser. No. 07/788,424).

Various surgical procedures can be performed to correct refractive errors or to treat eye diseases. The surgical beam can be directed to remove cornea tissue in a predetermined amount and a predetermined location such that the cumulative effect is to remove defective or non-defective tissue, or to change the curvature of the cornea to achieve improved visual acuity. Excisions on the cornea can be made in any predetermined length and depth, and in straight line or in curved patterns. Alternatively, circumcisions of tissue can be made to remove an extended area, as in a cornea transplant. The invention can be used to excise or photoablate regions within the cornea, capsule, lens, vitreoretinal membrane and other structures within the eye.

The present invention provides an improved method of eye surgery which has accurate control of tissue removal, flexibility of ablating tissue at any desired location with predetermined ablation depth, an optically smooth finished surface after the surgery, and a gentle surgical beam for laser ablation action.

The details of the preferred and other embodiments of the present invention are set forth in the accompanying drawings and the description below. Once the details of the invention are known, numerous additional innovations and changes will become obvious to one skilled in the art. Nevertheless, it will be understood that various modifications may be made without departing from the spirit and scope or the invention. Accordingly, it is to be understood that the invention is not to be limited by the specific illustrated embodiment, but only by the scope of the appended claims.

It is an object of the invention to provide improved surgical techniques for performance of currently used operations in several areas of the eye, such as corneal, glaucoma, cataract, vitreal and retinal.

It is a further object to improve such current ophthalmic surgical procedures by reducing the ocular trauma and complications associated with them by performing surgery with laser radiation of lower energy, and higher power density, than currently used lasers.

It is another object to improve the results of and allow more reproducible performance of operations on the cornea, such as lamellar and penetrating keratoplasty, keratomileusis, keratotomy, both linear and lamellar, whether for therapeutic or refractive purposes.

It is a further object to reduce optical (refractive) errors by obviating the need for cumbersome and complicated mechanical devices (such as the mechanical microkeratome, cryolathe and BKS device) from said surgery.

It is a specific object to achieve the preceding objects by providing procedures to reduce myopia, hyperopia, astigmatism, irregular astigmatism, presbyopia, optical aberrations of the eye such as spherical aberration, or any combinations thereof in a manner that will improve results and reduce tissue damage.

It is an object to provide a method (laser microkeratome) for resecting from a cornea a parallel-faced lamellar disc (lamellar keratectomy) without refractive power whether for therapeutic or refractive surgery while eliminating the need for manual dissection or mechanical microkeratome.

It is a further object to use the said laser microkeratome to perform on the cornea a lamellar keratectomy with non-parallel faces, isolating or removing from the cornea a lamellar refractive lens, such that the cornea is left with a new anterior surface with different curvature, thereby allowing the direct correction of optical refractive errors.

It is a further object of the invention to use the said laser microkeratome to perform on the cornea a lamellar keratectomy of varying diameter, whose thickness may be constant or varied, such that following the ablation, with the lamellar disc in its original bed, hyperopia, with or without astigmatism, is corrected.

It is an object of the invention to provide a means of performing keratomileusis-in-situ with increased accuracy and precision while eliminating one or both steps of mechanical microkeratome resection on the patient's cornea.

It is an object to accomplish performance of a variety of corneal surgical procedures while providing for a relatively normal anterior corneal structure in the critical central optic area at the conclusion of the procedure.

It is an object to accomplish the above by visible or infrared wavelength laser irradiation to the cornea, using any commercially available laser, with or without a beam control scanner, except in the case of keratomileusis-in-situ, where an ultraviolet laser may be used.

It is a further object to allow performance of glaucoma operations with increased accuracy and precision, such as sclerostomy, trabeculectomy, trabeculoplasty and iridotomy while reducing shock waves to the interior of the eye.

It is an object of the invention to allow the surgeon to open the anterior capsule of the lens of the eye in a controlled manner such that a smooth and regular opening (capsulorhexis), with predictable dimension, is achievable, thereby allowing safer insertion and fixation of intraocular lenses during cataract surgery.

It is a further object of the invention to alter the viscoelastic properties of the lens or to ablate it partially or entirely using laser radiation which reduces shock waves within the eye, thereby reducing complications.

It is a further object of the invention to alter the viscoelastic properties of the lens or to ablate it partially such that the anterior or posterior lens capsule undergoes a specific shape or curvature change calculated to correct optical refractive errors of the eye.

It is a further object of the invention to allow opening of the posterior capsule of the lens (posterior capsulectomy) without opening the eye, and to do so in a manner which reduces the shock waves and complications typically associated with such a procedure.

It is an object of the invention to allow the sectioning or ablation of pathologic membranes within the vitreous cavity of the eye with less trauma, thereby allowing the surgeon to operate closer to the delicate retina than heretofore possible.

It is an object of the invention to allow destruction of sub-retinal membranes or blood vessels while minimizing damage to the retina itself by focusing the radiation behind the retina and ablating the pathologic tissue while sparing the overlying retina.

BRIEF DESCRIPTION OF THE DRAWINGS

Like reference numbers and designations in the various drawings refer to like elements.

FIG. 15A1 is a frontal view of the lens of the eye demonstrating a smooth circular opening (capsulorhexis) made by a gentle laser beam and an irregular opening made by a laser with less refined cutting ability.

FIG. 15B1 demonstrates, as an elevation in section, a laser anterior capsulectomy.

FIG. 15C1 is an elevation in section describing phacorefractive surgery.

FIG. 15D1 demonstrates ablation of the lens substance to correct refractive errors.

FIG. 15E1 demonstrates laser ablation of a vitreous membrane.

DETAILED DESCRIPTION OF THE INVENTION

Figure 1A:
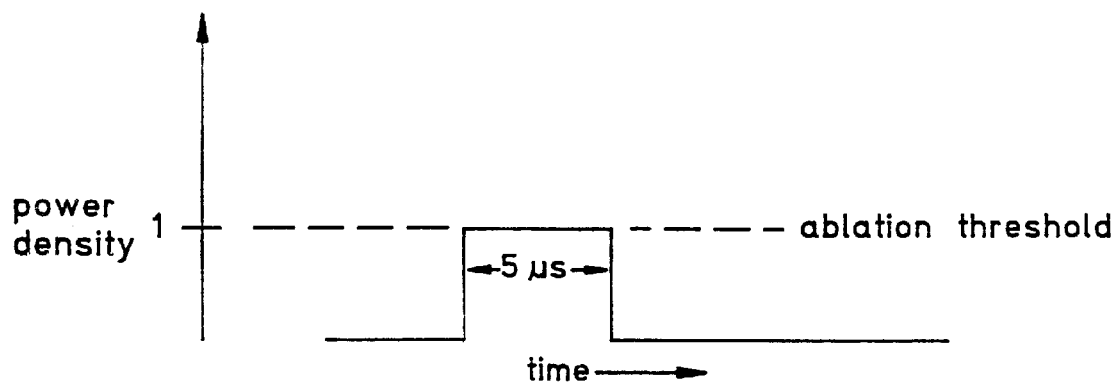
FIG. 1A is a diagram showing the power density of a square laser pulse versus time for a 5 ns pulse.

Throughout this description, the preferred embodiment and examples shown should be considered as examples, rather than limitations on the method and apparatus of the present invention.

The laser apparatus and method disclosed in this invention is for achieving two principal objectives:

(1) The damage zone around the material ablated by the inventive laser system must be substantially reduced in comparison to prior art laser systems.

(2) For each laser pulse deposited in the eye, a definite predetermined depth or volume of tissue is to be ablated. The ablated depth per laser pulse must be controllable and about 5 $\mu$m or less, and preferably about 0.5 $\mu$m or less.

To achieve these objectives, the present invention uses short duration laser pulses from about 10 femtoseconds to 2 picoseconds to reduce inflicted damage to target tissues.

The preferred laser system uses lasting ions such as titanium, chromium or neodymium (for example, $Ti_3:Al_2O_3$, $Cr:LiSrAlF_6$, Nd:YLF, or similar lasers), with a preferred wavelength of about 400 nm to about 1900 nm. The laser beam cross-sectional area is preferably about 10 μm in diameter. The importance of these characteristics is explained below.

Laser Pulse Duration

A fundamental problem of prior art ophthalmic surgical laser systems is that such systems fail to adequately take into account the interaction of the laser beam with organic tissue in the ablation process particularly when using relatively transmissive laser wavelengths. Laser ablation occurs when the laser beam intensity, or energy level, is increased beyond a certain threshold level, causing dielectric breakdown. However, the actual ablation conditions vary depending on the characteristics of a wide range of laser parameters and the composition of the material to be ablated. When laser energy is absorbed in an organic material, on the most basic level, the electronic configuration or the target polymer molecules makes a transition to one of its excited electronic states. Each polymer is made of hundreds or more of sub-units of smaller molecules called monomers. The monomers are made of even smaller units of radicals consisting of combinations of hydrogen, carbon, oxygen, and nitrogen atoms. Depending on the energy level of the laser photons, a polymer can be broken into constituent monomers, radicals, or ionized atoms.

For a laser having a wavelength near about 830 nm, a single laser photon is not sufficiently energetic to break any molecular bond. Breaking such a bond is a highly non-linear multi-photon process. After absorbing an initial photon, a molecule is promoted to an excited electronic state configuration, with its electrons in higher energy orbits. This state will decay, or "relax", if additional photons are not absorbed to maintain the excited electronic state configuration.

As the laser beam intensity increases further towards the ablation threshold, additional photons are absorbed, and the excited electron density reaches a critical volume density such that the electric orbitals can pair and transfer the sum or their energy to a single electron orbital. This process breaks the molecule into two or more pieces, and releases an energetic electron. At this point, the organic medium is damaged but not yet ablated.

With increased power levels of the laser beam, further photons are absorbed, and the excited electron density increases correspondingly. At the same time, the excited electrons migrate down the polymeric chain of the organic material, and spread towards the bulk volume with lower excited state density. The present invention recognizes that the excited state electronic orbitals are the means for energy storage that will eventually fuel the ablation process, and the electronic energy state migration process plays a key role in the dynamics controlling the initiation of the laser ablation.

Because photoablation requires multiple photons interacting with organic tissue molecules, 'ignition" or ablative action near the threshold condition is determined by a statistical process. That is, determination of the average etch depth or volume for laser beam energies near the ablation energy threshold are derived by measuring actual etch depth or volume after hundreds or sometimes thousands of laser pulses over the same location, and determining an average etch amount per pulse. On a single shot basis, however, the etch depth or volume could vary significantly, and most of the laser pulses may not ablate any material at all. In general, the ablation threshold for a particular wavelength is the total integrated energy required for 50% of laser pulses to have an effect.

Because of the statistical nature of laser pulse ablation, it is important to note that a reproducible etch depth or volume will not necessarily be attained at reduced levels of laser energy per pulse, especially when the energy level is close to being at an arbitrarily small value above the ablation energy threshold. Thus, in order to ensure a reliable etch depth or etch volume for each single laser pulse, the operating energy per pulse is conventionally set at a multiple of the ablation energy threshold level; a factor of 3 to 4 times the ablation energy threshold is usually considered sufficient to achieve satisfactorily results. For an excimer laser, the ablation threshold level is at about 50 $mJ/cm^2$; basically no ablative action is observed at a laser energy density below this threshold level. Accordingly, the typical energy density in an excimer surgical laser beam required for cornea ablation is about 150–250 $mJ/cm^2$.

Consider now the geometric distribution of the excited state orbitals in an organic material. As the laser light is absorbed in the organic material, by Beer's law the front surface where the material is first exposed encounters most of the laser photons, and the beam intensity decreases exponentially as it traverses deeper into the material. Hence, the spatial distribution of the excited state density also decreases accordingly, characteristic of the absorption coefficient of the material at the laser wavelength. It follows that the slope of the distribution curve of the excited state electron density is directly related to the absorption coefficient. Additionally, the steeper the slope of the excited state density distribution curve, the more spatially localized is the excited state density.

Thus, to maintain a small laser beam interaction point (e.g., about 1 μm to about 30 μm, and preferably about 10 μm), the slope of the excited state density distribution curve must be steep. To obtain a steep slope, the pulse width of the impinging laser beam should be kept narrow.

Figure 1B:
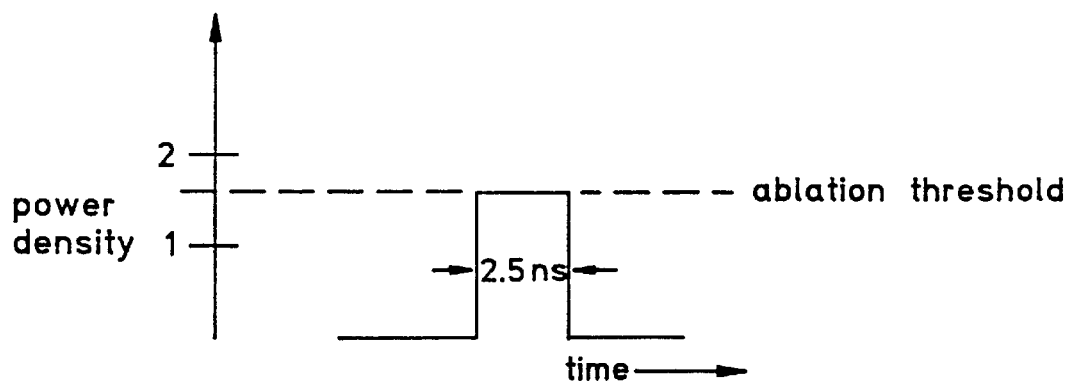
FIG. 1B is a diagram showing the power density of a square laser pulse versus time for a 2.5 ns pulse.

It is known that if ablation is found to occur at a particular laser peak power, narrowing the laser pulse increases the ablation threshold. For example, FIG. 1A is a diagram showing the power density of a square laser pulse versus time for a 5 ns pulse. If the ablation threshold is found to occur at a particular power density (arbitrarily considered to have a value of "1" FIG. 1A), then a higher ablation threshold is required when the pulse is narrowed. That is, total integrated energy of the shorter laser pulse must approach the total integrated energy of the longer laser pulse. However, it is also known that having the pulse duration does not require a doubling of the power density of the pulse. For example, FIG. 1B is a diagram showing the power density of a square laser pulse versus time for a 2.5 ns pulse. The ablation threshold is less than twice the ablation threshold of a 5 ns pulse.

Empirical results obtained from materials damage indicate that a particular ablation threshold can be reached with a pulsed laser beam 100 times shorter in duration than a longer duration pulse when the total integrated energy of the shorter laser pulse is at about 10% of the total integrated energy of the longer pulse.

Figure 2:
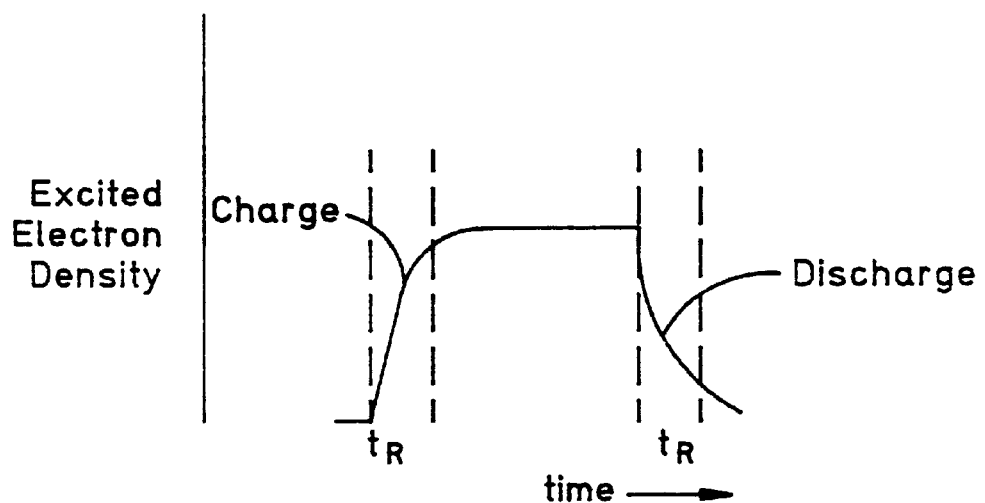
FIG. 2 is a diagram showing the excited state electron density of eye tissue at a laser beam interaction point.

Conventional teaching requires an increase in the ablation threshold energy density as pulse widths are decreased. However, it has been recognized in the present invention that the reason having the pulse width of a laser does not require a doubling of the ablation threshold energy density is related to the build-up and relaxation of the excited state electron density. FIG. 2 is a diagram showing the excited state electron density of eye tissue at a laser beam interaction point. The diagram shows that the excited state electron density is related to the energy density of the incident laser beam. As photons from a laser beam interact with tissue, the electron state of the molecules undergo "charging" to a steady state. The "charging" time $t_R$ is related to the electron migration rate. The discharge time is also equal to $t_R$. The charge/discharge time $t_R$ is approximately 0.5 to 1 picoseconds.

After the initial photons of a laser pulse charge the excited state electron density to a steady state, the remaining photons of the pulse have essentially no effect on such density. The steady state arises because energy migrates away from the beam interaction point. When using longer duration pulses, the energy migration process is counter-balanced by additional laser beam pumping to build up the critical excited state electron density. However, with a longer laser pulse, the excited state orbitals diffuse from the laser interaction point into the depth of the material (along the laser beam direction). Hence, the excited state distribution curve will have less steep a slope compared to the curve from a shorter pulse. The present invention recognizes that the depth of the tissue layer which has sufficient excited state orbitals to satisfy the ablation threshold condition will be correspondingly deepened. Therefore, the damage inflicted by a longer duration laser pulse is more extensive than the damage inflicted with a shorter duration pulse.

As noted above for a laser pulse having a low energy density, a longer pulse duration is required to achieve sufficient photon interactions to charge the excited state electron density to a steady state. Conversely, for a laser pulse having a shorter duration, a higher energy density is required. However, because of the higher energy density, more photon interactions per unit of time occur, thereby more rapidly charging the excited state electron density to the steady state. Less energy migrates away from the laser interaction point. Consequently, the total integrated energy of a narrower pulse need not be as great as the total integrated energy of a longer pulse to achieve the ablation threshold.

Figure 1C:
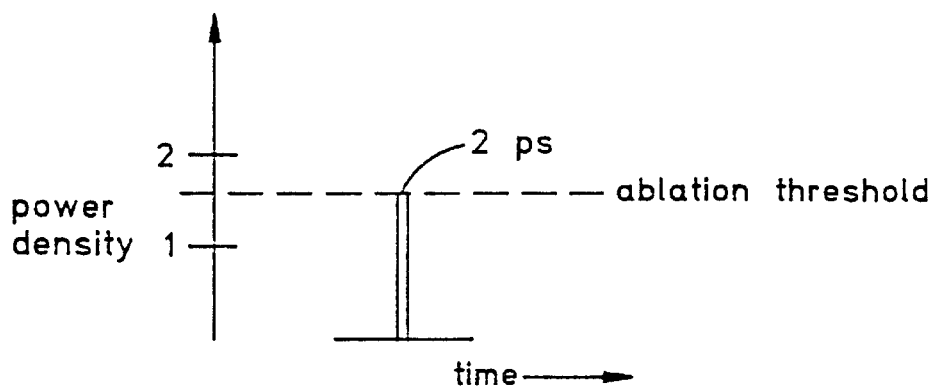
FIG. 1C is a diagram showing the power density of a square laser pulse versus time for a 2 ps pulse.
Figure 3:
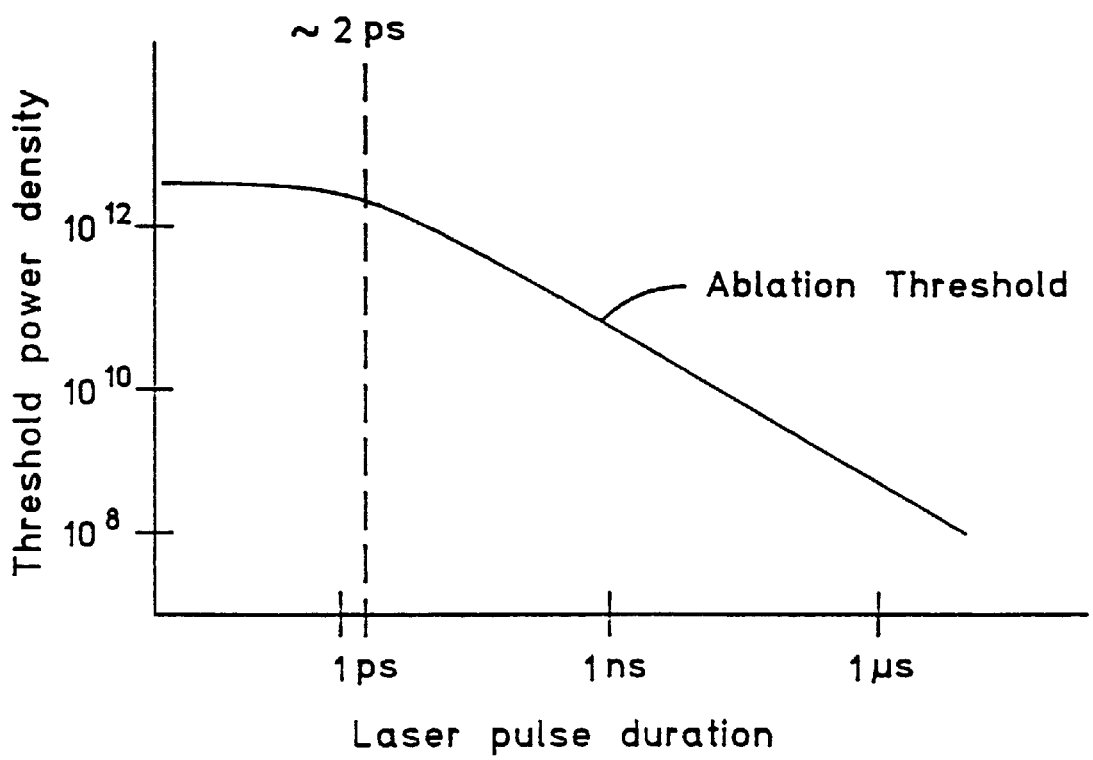
FIG. 3 is a diagram showing eye tissue ablation energy threshold versus pulse width.

Importantly, it has been discovered in the present invention that the power density for the ablation threshold reaches an approximately constant level as the laser pulse width decreases and closely approaches the charge/discharge time $t_R$. For example, as shown in FIG. 1C, a 2 picosecond pulse may have about the same ablation threshold as a much shorter pulse. FIG. 3 is a diagram showing eye tissue ablation energy threshold versus pulse width. As the laser pulse width reaches about 2 picoseconds, and the energy density of the beam is about $1.0 \,\mu J/(10 \,\mu m)^2$ for an 830 nm wavelength, the number of photons is sufficient to maintain a steady state excited state electron density without significant decay. This relationship between pulse duration and constant ablation threshold has been found to exist from about 2 picoseconds down to at least 10 femtoseconds.

Thus, ablation can be achieved at a low ablation threshold energy using such extremely short duration laser pulses. Further, tissue damage from acoustic shock and kinetic action from dissociated matter is directly proportional to energy deposited at the laser interaction point. If the ablation threshold is achieved at less than the total pulse energy, the remaining energy in the pulse is completely absorbed by the generated plasma, thereby contributing to the explosive effect of the tissue ablation. Both acoustic shock and kinetic action are decreased by reducing the pulse duration.

Figure 4:
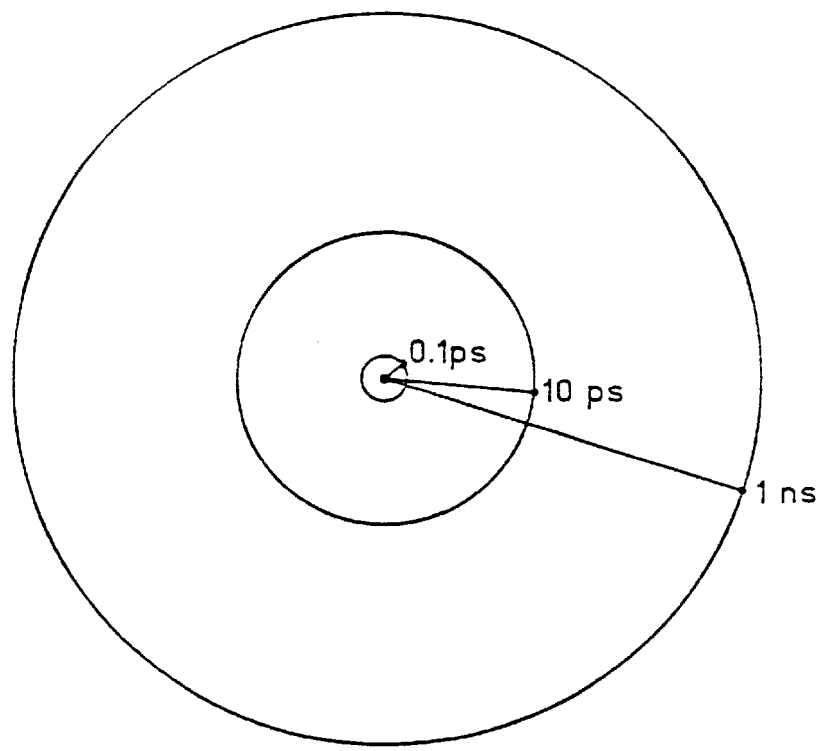
FIG. 4 is a diagram showing the relative diameters of tissue regions removed by laser pulses at the ablation threshold for pulses of approximately 1 ns, 10 ps, and 1 ps duration.

Another benefit from reducing the pulse duration is limitation of damage tissue surrounding the laser interaction point due to energy migration. FIG. 4 is a diagram showing the relative diameters of tissue regions removed by laser pulses at the ablation threshold for pulses of approximately 1 nanosecond, 10 picoseconds, and 0.1 picosecond duration. As can be seen, the range of tissue removal and surrounding tissue damage is substantially less for the shorter pulses (the volume of tissue removed is proportional to energy deposited, which falls off from the center of the interaction point proportionally to the radius cubed).

Transmissive Wavelengths

In order to perform intraocular surgical procedures, the laser beam necessarily must pass through overlying tissue to the desired location without damage to the overlying tissue. Accordingly, the illustrated embodiment of the present invention uses an 830 nm wavelength for the laser beam, which is generally transmissive in eye tissue. Such a wavelength can be generated in known fashion from a broad gain bandwidth (i.e., $\Delta\lambda > \sim 1$ mm) laser, using lasing ions such as titanium, chromium or neodymium (for example, $Ti_3:Al_2O_3$, $Cr:LiSrAlF_6$, Nd:YLF, or similar lasers). One such laser is described in U.S. patent application Ser. No. 07/740,004, filed Aug. 2, 1991, entitled "Two Dimensional Scanner-Amplifier Laser" and assigned to the assignee of the present invention.

Other wavelengths could be used as desired, since absorption and transmission in the eye is a matter of degree. Thus, less transmissive wavelengths can be used for procedures at or near the front of the eye, such as the cornea. In general, acceptable wavelengths include the ranges of about 400 nm to about 1900 nm, about 2.1 $\mu$m to about 2.8 $\mu$m, and longer than about 3.1 $\mu$m.

Figure 5:
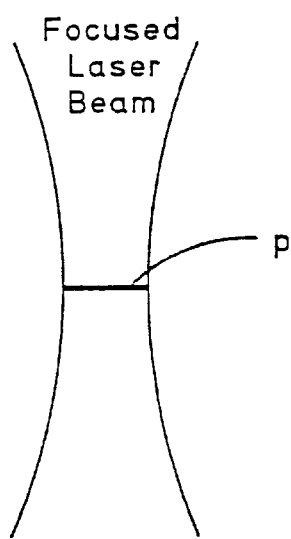
FIG. 5 is a diagram showing the interaction point of a laser beam.

Because of the preferred transmissivity of the laser beam, and the requirement that a threshold energy density be achieved to ignite ablation, the interaction "point" (generally, it is actually a planar region) of the laser beam can be focused quite tightly. FIG. 5 is a diagram showing the interaction point P of a laser beam. The portion of the beam above and below the interaction point P lacks sufficient energy density to ignite photoablation. Hence, those portions of the laser beam pass through the surrounding tissue without causing damage. Where the beam is focused most tightly (i.e., the focal point), the energy density is sufficient to initiate ablation.

Size of the Lazer Interaction Point

Another way to reduce the shock to the eye is by using a smaller beam area at the interaction point to reduce the intergrated recoil forces. Consequently, the laser beam cross-sectional area of the invention at the interaction point is preferably about 10 $\mu$m in diameter. The preferred beam size of the invention contrasts with current excimer laser surgical systems, which subject an ablation zone to a surgical beam that is typically 4–6 mm in diameter.

The beam diameter can be varied to any tolerable achievable smaller or larger dimension, as required by the particular type of surgery. In particular, a range of about 1 $\mu$m to about 30 $\mu$m is preferred.

The Inventive Apparatus

Figure 6:
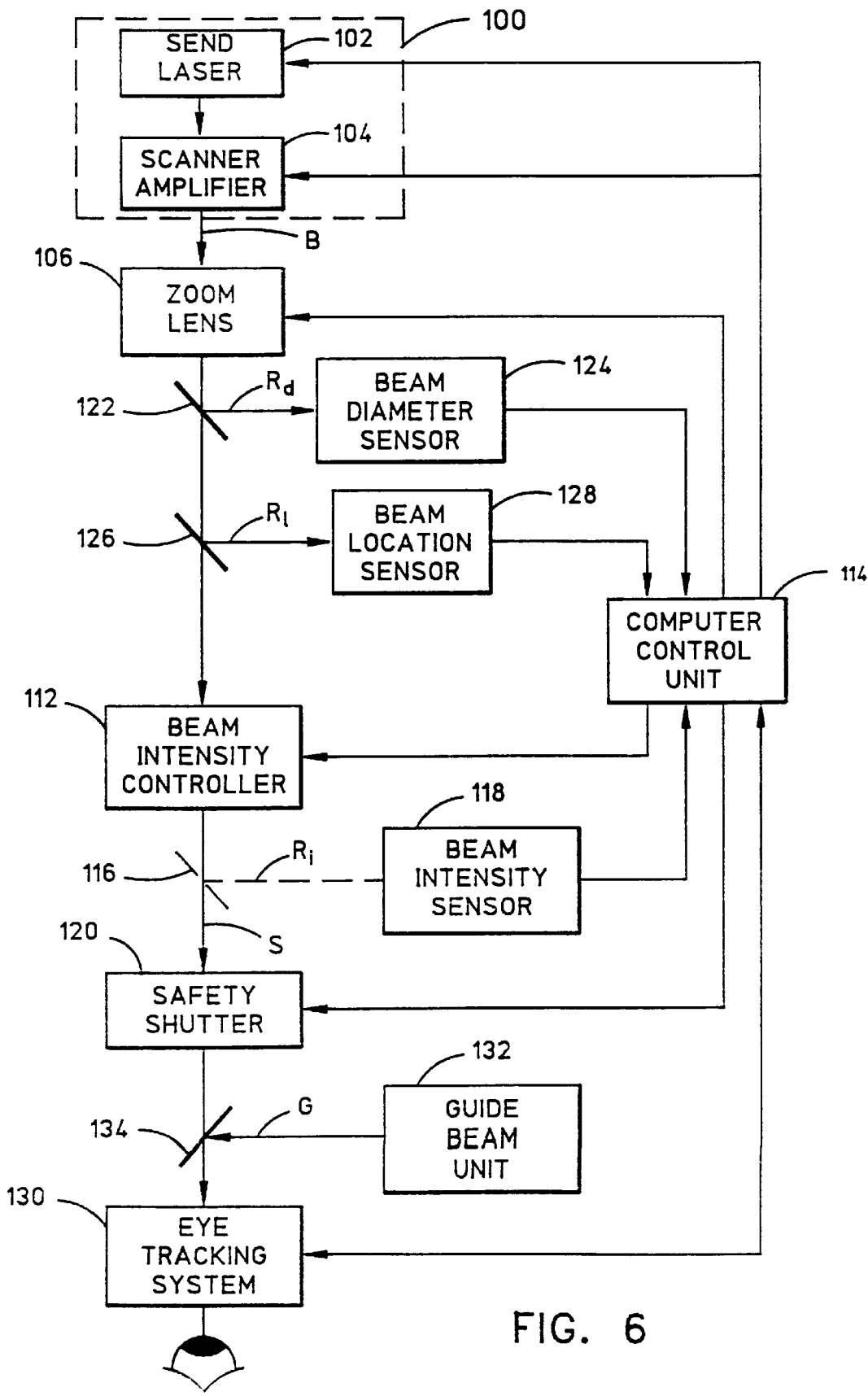
FIG. 6 is a block diagram of the preferred embodiment of the inventive apparatus.

Each laser pulse of the type described above is preferably directed to its intended location in or on the eye through a laser beam control means, such as the type described in the co-pending, commonly-owned U.S. patent application Ser. No. 07/788,424. FIG. 6 shows a block diagram of such a laser and control system.

More particularly, FIG. 6 shows a laser unit 100 of generating an initial laser beam B. The laser unit 100 is of the type that can output a beam rapidly deflectable or scannable under electronic control in two dimensions to any location in an area defined by orthogonal X and Y axes. One such laser unit is described in detail in the co-pending, commonly-owned patent application for invention entitled "Two Dimensional Scanner-Amplifier Laser" (U.S. patent application Ser. No. 07/740,004), which is hereby incorporated by reference.

The initial laser beam B comprises a sequence of laser pulses having a pulse repetition rate of about 100 to 100,000 pulses per second. The actual number of laser pulses used for a surgery is determined by the amount of tissue to be removed.

In a preferred embodiment, the laser unit 100 includes a seed laser 102 and a scanner-amplifier laser 104. Preferably, the lasing ion in the solid state laser crystal in both the seed laser 102 and the scanner-amplifier 104 is titanium (such as in $Ti_3:Al_2O_3$, for example).

After emerging from the laser unit 100, the laser beam B passes through a computer-controllable, motorized zoom lens 106, which provides control over the diameter of the laser beam B. In practice, the zoom lens 106 may be placed in a number of suitable positions along the optical path of the laser beam between the laser unit 100 and a target. The motor actuation of the zoom lens 106 may be by any known means, such as electrical gear drives or piezoelectric actuators.

While the laser beam B could be used directly for surgical procedures, in the preferred embodiment the entire surgical laser apparatus includes a number of control and safety systems. In particular, the present invention includes means for monitoring and controlling the intensity of the beam, means for blocking the surgical beam in the event of a malfunction, means for monitoring and controlling the laser beam diameter and intensity profile, and means for verifying the two-dimensional (X and Y axes) scan position of the surgical beam.

Referring again to FIG. 6, the laser beam B passes through a beam intensity controller 112, the output of which is the surgical laser beam S. The beam intensity controller 112 permits regulation of the energy of each laser pulse so that the etch depth of each pulse may be precisely controlled. In the preferred embodiment, the beam intensity controller 112 is an electro-optical filter, such as an electrically activated Pockels cell in combination with an adjacent polarizing filter.

In the preferred embodiment, the beam intensity controller 112 is coupled to a computer control unit 114, which is suitably programmed to vary the intensity of the output surgical laser beam S as required for a particular surgical procedure. The degree or beam retardation as a function of applied electrical signal can be ascertained by standard calibration techniques. The preferred location of the beam intensity control unit 112 is as shown in FIG. 6. However, the beam intensity control unit 112 can be placed at several suitable locations in the beam path between the laser unit 100 and a target. In the preferred embodiment, the intensity of the surgical beam S is regulated to have an ablation energy density of less than or equal to about 5 $\mu J/(10\ \mu m)^2$.

The present invention optionally provides for positive feed-back measurement of the beam intensity. A partially transmissive beam-splitting mirror 116 is placed after the beam intensity controller 112, and the reflected beam $R_i$ is directed to a beam intensity sensor 118. The beam intensity sensor 118 may be simply a photocell, although other elements, such as focussing optics, may be included. By monitoring the electrical output of the beam intensity sensor 118 with the computer control unit 114, the intensity of the surgical laser beam S can be positively measured to verify the proper operation of the beam intensity controller 112. The output of the beam intensity sensor 118 as a function of intensity of the surgical laser beam S can be ascertained by standard calibration techniques.

The inventive system also preferably includes a safety shutter 120, which is coupled to the computer control unit 114. The safety shutter 120 may be, for example, a mechanically-actuated shutter operated in a "fail-safe" mode. For example, the safety shutter 120 may include a solenoid-actuated shield that is positively held open by application of electrical energy to the solenoid. Upon command of the computer control unit 114, or failure of the entire system, electrical energy to the solenoid is cut off, causing the solenoid to retract the shield into position to block the path of the surgical laser beam S. The safety shutter 120 is also useful for temporarily blocking the laser beam S while changing the position of the patient's eye or of the beam itself, without turning the laser beam S completely off.

In an alternative embodiment, the safety shutter 120 may include a Pockels cell and polarizer configured as a light valve, with the Pockels cell biased with respect to the polarizer by application of an electrical voltage such that maximum light is normally transmitted by the combination. Cessation of the applied voltage will cause the output of the Pockels cell to become polarized orthogonal to the transmission direction of the polarizer, hence blocking the surgical laser beam S. Using this alternative configuration, the safety shutter 120 and the beam intensity controller 112 may be combined into a single unit.

Any other suitable means for quickly blocking the surgical laser beam S on command or in the event of system failure may be used to implement the safety shutter 120. In practice, the safety shutter 120 may be placed in a number of suitable positions along the optical path of the laser beam between the laser unit 100 and a target.

To control beam diameter, the inventive system provides a partially transmissive beam-splitting mirror 122 that reflects part of the beam $R_4$ to a beam diameter sensor 124. In practice, the beam diameter sensor 124 may be placed in a number of suitable positions along the optical path of the laser beam between the laser unit 100 and a target. The beam diameter sensor 124 preferably includes at least a diverging (concave) lens and a converging (convex) lens configured as a magnifying telescope (i.e., the two lenses have a common focal point, with the focal length $f_2$ of the converging lens being greater than the focal length $f_1$ of the diverging lens, and having optical centers aligned with the incident laser beam in its un-deflected position). The incident beam $R_4$ enters the diverging lens and exists the converging lens. Such a configuration of lenses, while enlarging the incident beam, will also reduce the scan angle of the exiting beam.

The resulting enlarged beam is directed to a high sensitivity, low contrast imaging device, such as a charge-coupled device (CCD) camera. The converging and diverging lenses are chosen to expand the incident beam $R_4$, so that the largest possible diameter for the beam just fits within the imaging device. In the preferred embodiment, the size of the beam is determined by periodically addressing a central row and a central column of the imaging device and counting the number of pixels on each sampled axis that have been illuminated. By comparing the diameter of the beam in both the X and Y directions, the beam diameter sensor can determine whether the incident laser beam B is approximately circular and has the desired diameter.

The beam diameter sensor 124 can also be used to determine the intensity profile of the laser pulses, since each pixel in the beam diameter sensor 124 can generate an output indicative of the intensity of light incident to the pixel. By comparing pixel values from radially symmetric points in the pixel array, it can be determined if an incident laser pulse or series of pulses has the desired radially symmetric intensity profile, or if the pulses have developed "hot spots" or out-of-range intensity values.

The output of the beam diameter sensor 124 is coupled to the computer control unit 114. The computer control unit 114 is in turn coupled to the motorized zoom lens 106, which provides control over the diameter of the laser beam B. The computer control unit 114 is suitably programmed to vary the diameter of the laser beam as required for a particular surgical procedure. The output of the beam diameter sensor 124 as a function of beam diameter can be ascertained by standard calibration techniques.

This configuration provides positive feed-back of the beam diameter emanating from the laser unit 100. If the beam diameter sensor 124 detects an out-of-range beam (either diameter or intensity profile), the computer control unit 114 can take appropriate action, including activation of the safety shutter 120.

To verify the X-Y scan position of the laser beam, the inventive system provides a partially transmissive beam-splitting mirror 126 that reflects part of the beam energy Ri to a beam location sensor 128. The beam location sensor 128 preferably includes at least a converging (convex) lens and a diverging (concave) lens configured as a reducing telescope (i.e., the two lenses have a common focal point, with the focal length $f_2$ of the diverging lens being greater than the focal length $f_1$ of the converging lens, and having optical centers aligned with the incident laser beam in its un-deflected position). The incident beam Ri, enters the converging lens and exits the diverging lens. Such a configuration of lenses, while reducing the incident beam, will also increase the scan angle of the exiting beam.

The resulting increased-scan angle beam is directed to a silicon photo-detector, such as the position sensing detector, model DLS-20 manufactured by UDT Sensors, Inc. of Hawthorne, Calif. The photo-detector provides a voltage reading with respect to the two-dimensional (X-Y) position of an illuminating spot at the detector surface. The output of the beam location sensor 128 is coupled to the computer control unit 114. Calibration of the voltage reading generated from the un-deflected incident beam position on the photo-detector will indicate the origin of the laser beam in the X-Y scan plane. Any deflection of the beam from the origin will generate voltage readings indicative of the spot on the photo-detector surface illuminated by the laser beam. These voltage readings are calibrated against the indicated location of the surgical beam as set by the computer control unit 114. During operation, the output of the beam location sensor 128 would be sampled periodically (for example, about 1,000 times per second) and compared to a prepared calibration table in the computer control unit 114 to determine if the actual beam position matches the indicated position.

This configuration provides positive feed-back of the beam position emanating from the laser unit 100. If the beam locator sensor 128 detects an out-of-position beam, the computer control unit 114 can take appropriate action, including activation of the safety shutter 120.

Thus, the preferred embodiment of the inventive surgical laser apparatus provides for safe and effective surgery by continuously monitoring all aspects of the condition of the surgical laser beam S, including beam intensity, diameter, and X-Y scan position.

In order to provide accurate positioning of the surgical laser beam S, an eye tracking system 130 is placed in the path of the surgical laser beam S, preferably in close proximity to a target eye. The eye tracking system 130 monitors movement of a patient's eye and adjusts the position of the surgical laser beam S to compensate. Such tracking may be accomplished by providing fiducial marks on the eye and optically tracking movement of said fiducial marks. Deflectable mirrors may then be used to steer the surgical laser beam S. An example of one such system is described in co-pending U.S. patent application Ser. No. 07/788,424, which description is hereby incorporated by reference.

In order to improve the ease of use of the present invention, and to ensure proper alignment of the surgical laser beam S with respect to a target eye, the present invention includes a guide beam unit 132. The guide beam unit 132 includes a low-power laser with an output of preferably less than 1 milliwatt at initial output and preferably attenuated to the microwatt level for safe usage for direct viewing. The low-power laser generates a guide beam which is conditioned optically so that it is aligned with the surgical laser beam S and can be used as a indicator of the location of the surgical laser beam S. Additionally, the guide beam can be used as an element for the alignment of a patient's eye in preparation for surgical procedures.

Example Surgical Procedures

The laser surgical system of the present invention can perform numerous types of surgical procedures on the eye. At the beginning of a surgical procedure, the focal point of the surgical laser beam is focussed at a starting reference location, preferably in the vicinity of the point of surgery. After adjustment of the target tissue location, such as by use of a guide beam, and at the satisfaction of the surgeon, the eye tracking system 130 is activated. Any eye movement thereafter will be compensated for by a corresponding automatic adjustment of the laser beam position.

According to the prescription of the surgeon, the inventive system can perform any and all of the following procedures:

(1) The inventive system can easily create straight line and curved-line excisions, of any predetermined length and depth, at any location determined by a surgeon.

Figure 7:
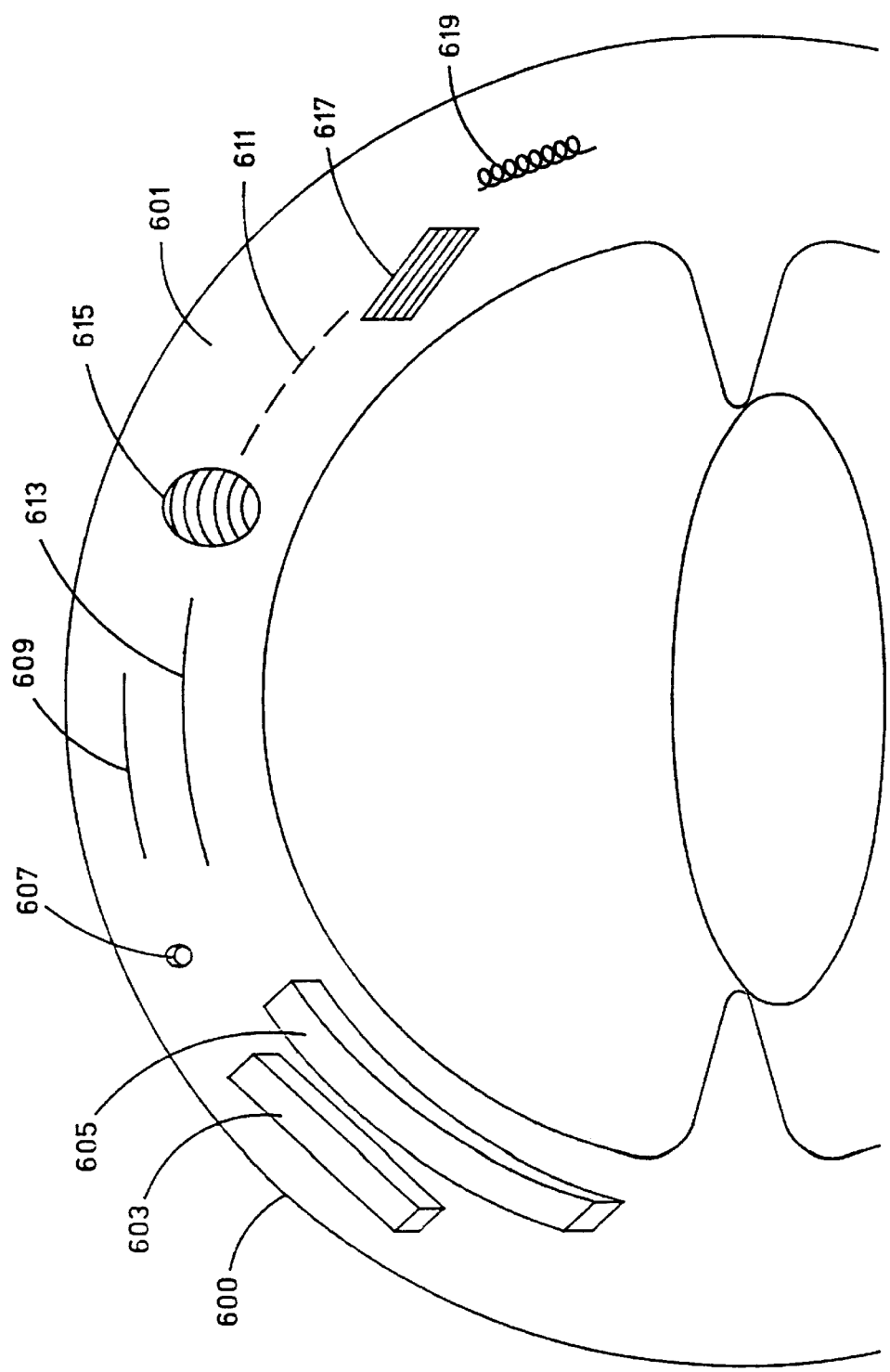
FIG. 7 is a cross-sectional side view of a cornea showing some of the resulting incisions which can be formed in the stromal by the present invention.

FIG. 7 illustrates some of the resulting excisions which can be formed in the stroma 601 of an eye 600. The excisions shown in FIG. 7 are merely intended to illustrate a limited number of examples of the types of excisions that can be made using the invention, and are not intended to demonstrate any particular surgical procedure, or to imply that the illustrated excisions are the only relevant types of excisions that can be easily made in accordance with the present invention. The excisions illustrated in FIG. 7 include a straight channel 603, a curved channel 605, a point 607, a line 609, an interrupted line 611, a curve of varying depth 613, a circular area 615, a square or parallelepiped area 617, or a spiral 619. The invention encompasses any combination of such excisions.

Figure 8B:
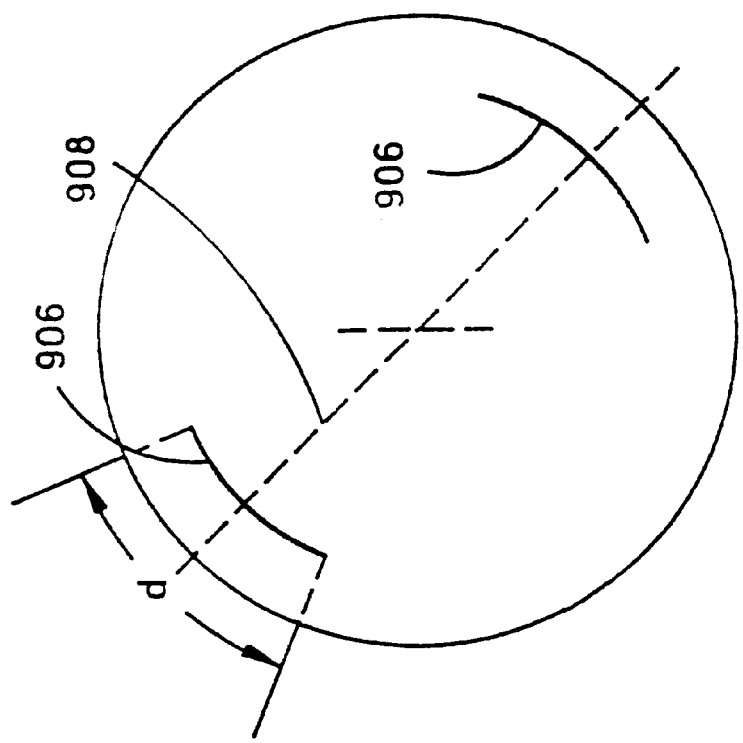
FIG. 8B is a front view of a cornea, showing the use of the present invention to make transverse excisions on the cornea.
Figure 8A:
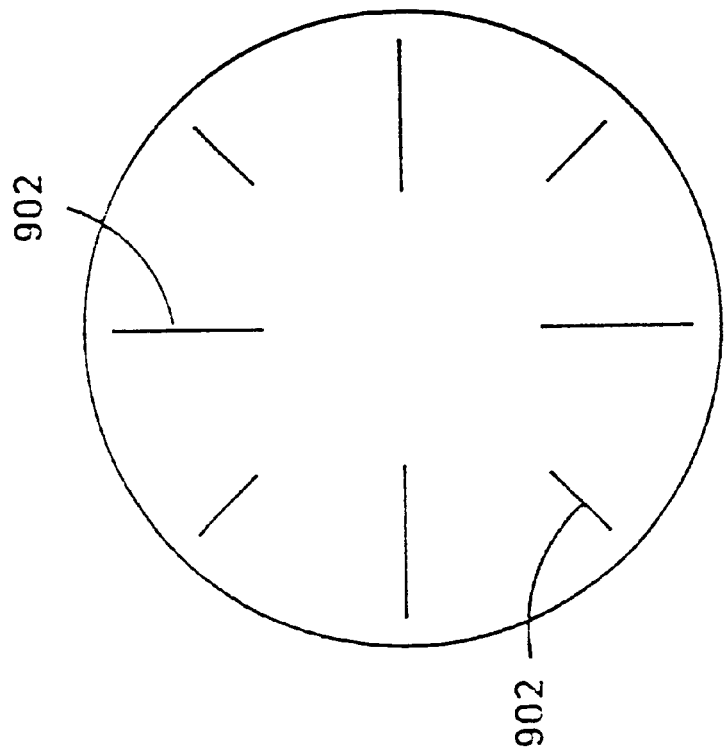
FIG. 8A is a front view of a cornea, showing the use of the present invention to make radial excisions on the cornea.

As illustrated in FIG. 8A, multiple radial cuts 902, equal or partially equal in excision length and with an angular separation between cuts, can be made on the cornea with the present surgical system. An excision can be made by directing the surgical laser beam S to a predetermined location at the cornea, and removing the desired amount of tissue by controlling the laser beam energy dosage. The present invention provides options for making an excision with either a wide excision width by using a larger beam spot size on the cornea surface, or a fine excision by using a more focussed beam spot. With the present invention, the depth of each cut can be varied over the length of a predetermined excision.

The invention can also easily generate arcuate cuts or transverse cuts ("T-cuts"), as shown in FIG. 8B. By directing the surgical laser beam S to make a pair of opposing curved excisions 906 along an axis 908 relatively to the center of the eye, the refractive power of the eye is decreased along the axis. The exact length d and the location of the excision can vary according to the amount of desired correction, in known fashion.

In general, excisions in the cornea can be made at effective locations for performing radial keratotomies or making T-cuts or arcuate cuts, to correct myopia, hyperopia, or astigmatism (regular or irregular).

The inventive system can also be used for procedures in cornea transplants. A circumcision of the cornea in any predetermined shape (e.g., circular, elliptical, polygonal, etc.) can be performed on the donor eye and the recipient's eye. In both cases, a computer control unit 114 (see FIG. 6), as described in the co-pending U.S. patent application Ser. No. 07/788,424, calculates the beam location based on the particular shape excision and the amount of laser energy needed to cut through the cornea.

(2) The second important type of laser-tissue interaction provided by the inventive system is area ablation, which permits direct sculpting of the corneal surface.

Figure 9A:
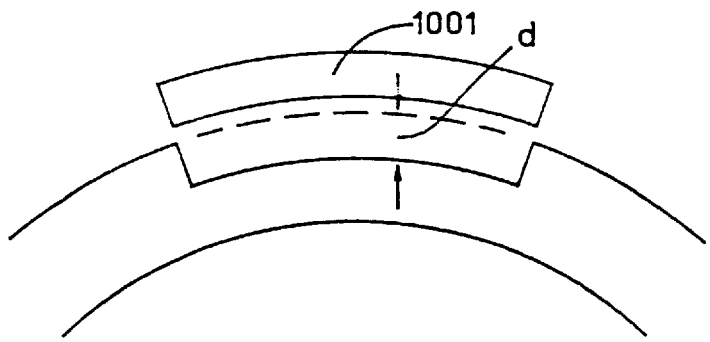
FIG. 9 is a cross-sectional side view of a cornea, showing the use of the present invention to remove tissue to a desired depth d over a predetermined area on the cornea, and showing an alternative method for performing a cornea transplant.

As illustrated in FIG. 9A, a local scar or infected tissue can be removed with the present invention. The defective tissue is removed to a desired depth d over a predetermined area on the cornea. A donor cornea cap 1001 can be cut and ablated ("sculpted") to the desired dimension, curvature, and thickness using the invention described in co-pending U.S. patent application Ser. No. 07/788,424. The cap piece is then transferred to the bared stromal bed and attached by suture, glue, or other appropriate means, in known fashion. The cap may be prepared in advance with an appropriate refractive power in a fashion similar to a contact lens. Such a cap can be used to change the refractive power of the eye to correct myopia, hyperopia, or astigmatism (regular or irregular).

Figure 9B:
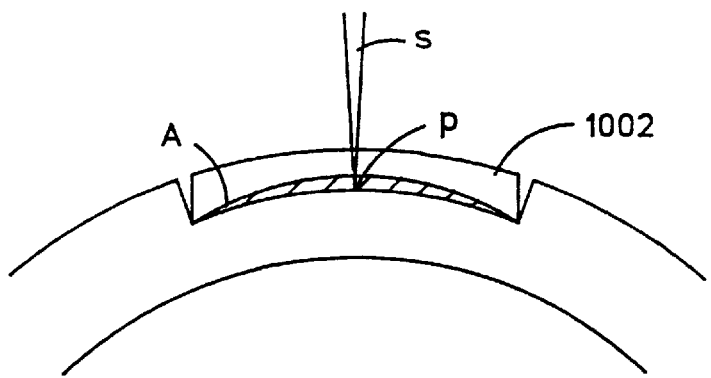

Referring to FIG. 9B, an alternative method is shown for performing a lamellar cornea transplant. Because the surgical laser beam S can be focussed through overlying tissue to an interaction point P, the surgical laser beam S can be used to ablate a layer of tissue beneath the surface of the eye to create an interior chamber A. Accordingly, using such "interior excision" or "intrastromal ablation", a section or segment of the cornea can be "excavated" in this manner, and then a circumferential ablation cut around the perimeter of the area can be made so that the entire segment can be lifted away from the eye as a cap 1002. If desired, the surgical laser beam S can be used to sculpt the back side of the material that will form the cap 1002, so as to change the refractive characteristics of the cap 1002. The cap 1002 can then be cut loose from the eye. If desired, further sculpting can be done directly on the exposed bed of the eye. Thereafter, the cap 1002 can be attached to the open ablated area by sutures or other known methods.

Another use of the invention is to produce standard at custom sculpted corneal caps in advance of need. The invention can be used on a donor cornea or a synthetic cornea substitute to ablate a desired profile to correct for myopia, hyperopia, or astigmatism. Such sculpted caps can then be attached to a properly prepared cornea, in known fashion.

Figure 10:
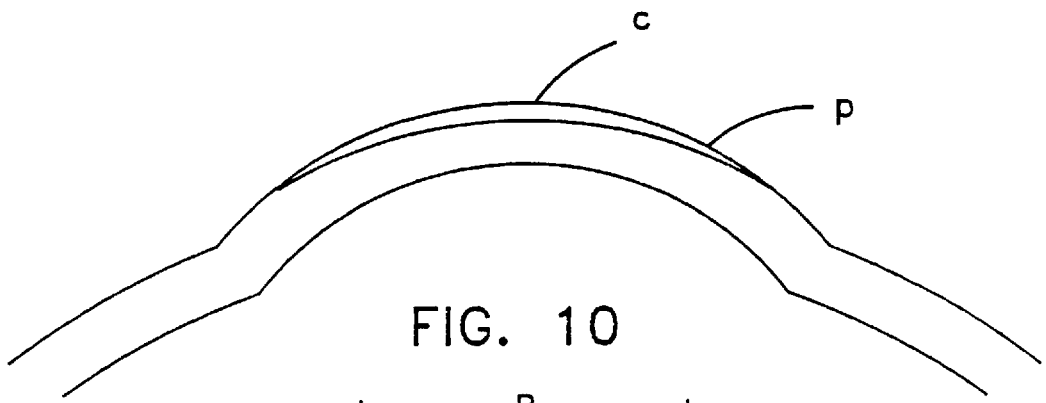
FIG. 10 is a cross-sectional side view of a cornea, showing the use of the present invention to correct myopia.

For myopia correction, as illustrated in FIG. 10, the curvature of the cornea can be reduced by selectively ablating the cornea such that more tissue is removed at the center portion C of the cornea, with a decreasing amount of tissue being removed towards the periphery P of the cornea. The inventive system can also be applied to ablate the corneal tissue near the surface of the cornea. The new desired profile of the eye may include Bowman's membrane and part of the stromal layer, depending on the amount of refractive correction required. As described in co-pending U.S. patent application Ser. No. 07/788,424, the computer control unit 114 provides for the sequence, location, and intensity of laser pulses to be deposited. The deposition pattern is preferably in accordance with the patterns discussed in the section 'Method of Depositing Laser Pulses' within the co-application.

Figure 12:
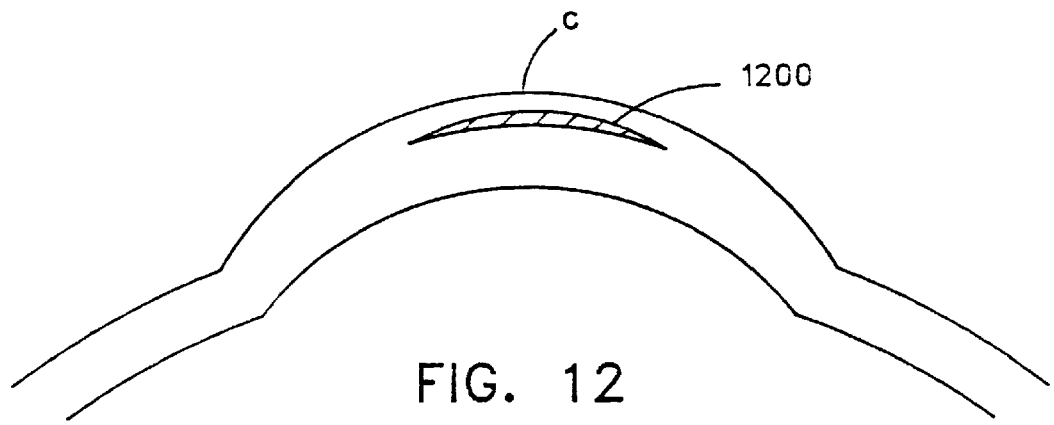
FIG. 12 is a cross-sectional side view of a cornea, showing the use of the present invention to correct myopia using an alternative method.

Another method for correcting myopia or hyperopia is to use the "interior excision" technique described above with respect to FIG. 9B. Referring to FIG. 12, correction of myopia may be performed by ablating material under the central portion C of the cornea. Depending on the amount of correction in the refractive power, the ablation gradient for the removed tissue varies. As the material overlying the chamber 1200 relaxes, it will reattach to bottom of the chamber, thus changing the curvature of the eye.

Figure 11:
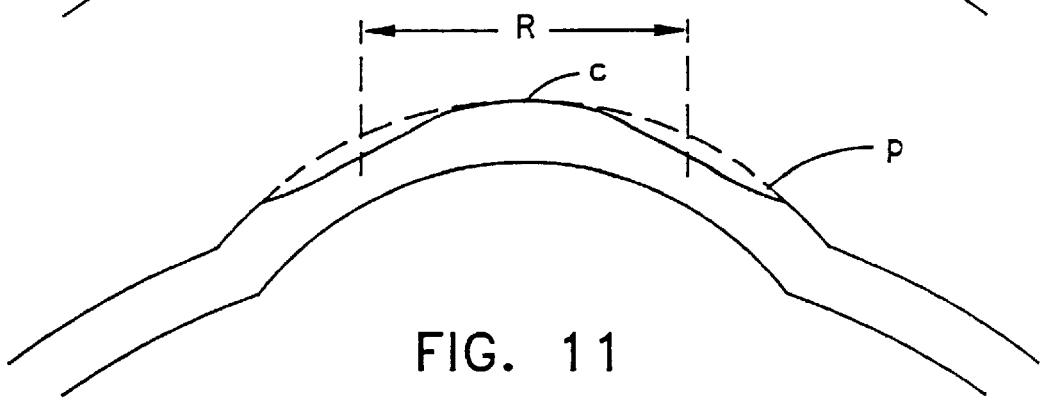
FIG. 11 is a cross-sectional side view of a cornea, showing the use of the present invention to correct hyperopia.

For hyperopia correction, as illustrated in FIG. 11, the objective is to increase the curvature of the eye. Corneal tissue is removed in an annular ring that is shallow near the center portion C of the cornea and increases in thickness towards the periphery P of the cornea. The depth of the removed tissue again decreases near the periphery of the eye for a smooth transition. Depending on the amount of correction in the refractive power, the etch gradient for the removed tissue varies. The size of the usable central region R varies depending on the amount of hyperopic correction.

Figure 13A:
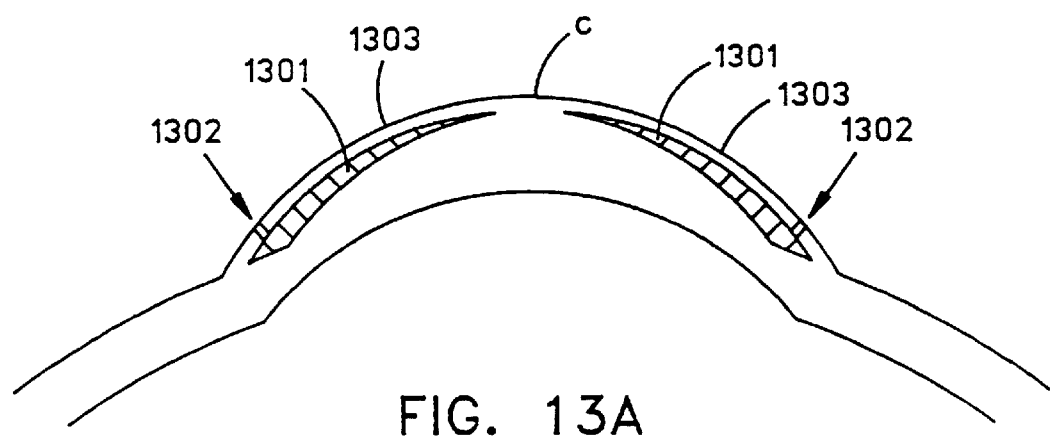
FIG. 13A is a cross-sectional side view of a cornea, showing the use of the present invention to correct hyperopia using an alternative method.
Figure 13B:
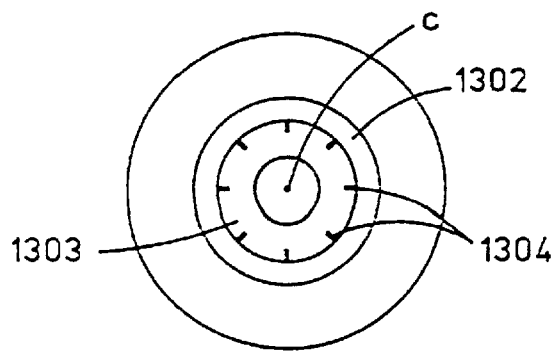
FIG. 13B is a top view of FIG. 13A, showing the use of peripheral radial cuts to help correct hyperopia.

Referring to FIG. 13A, hyperopia can also be corrected by ablating an annular chamber 1301 beneath the surface of the eye centered approximately on the center portion C of the cornea. Depending on the amount of correction in the refractive power, the ablation gradient for the removed tissue varies. After ablation of the chamber 1301, a circumferential excision 1302 is made around the bottom rim of the annular chamber 1301 to free an edge of the outer portion of the annular chamber 1301 from attachment to the eye, thereby creating a flap 1303. Generally, the flap 1303 will relax to the bottom of the chamber, the changing the curvature of the eye. However, if the flap 1303 is not thin enough to so relax, small perimeter radial cuts 1304 (shown in FIG. 13B) may be made in the edge of the flap 1303 to further relax the flap and cause it to adhere to the bottom of the chamber 1301 formed by the interior excision.

In addition to the above methods for correction of myopia and hyperopia, the invention may be used to correct regular or irregular astigmatism or complex refractive errors. The amount and distribution of tissue to be removed from various locations within the stroma is determined by the amount of correction required.

The invention is particularly useful for the correction of asymmetric refractive errors. Irregular distortions may result from poor matching of a cornea from a transplant, uneven suturing, or from imperfect refractive surgical procedures such as lamellar keratomileusis or epikeratophakia. The inventive system can direct the surgical laser beam to any desired location to sculpt the cornea according to a predetermined shape. The surgical laser beam thus can be applied to smooth out an irregular corneal profile.

(3) The third important type of laser interaction provided by the inventive system is intraocular excisions. The invention can be used to excise or photoablate regions with the cornea, capsule, lens, vitreoretinal membrane, and other structure within the eye.

For example, the present invention is useful for performing surgical procedures to correct glaucoma by creating one or more openings through the iris to release fluids from the posterior chamber which create undesirable pressure behind the cornea. In addition, one or more excisions may be created in the posterior or anterior capsule to permit removal of material from the capsule and to implant an intraocular lens (IOL) or any other lens-like material or structure which can be in fluid or gel form. By directing the laser focus at the lens of the eye, a cataractous lens can be ablated and liquified. Thus, the inventive procedure can be used prior to an IOL implant for cataract conditioning. Furthermore, portions of a retinal membrane which create tension on the retina may be cut to relive such tension. Also, portions of the retina may be operated upon to remove harmful tissue. Accordingly, the invention precisely controls and determines the location of the interaction point of a surgical laser beam, and controls the shape of cornea during the ophthalmic surgery.

Additional Embodiment

Another embodiment of an ophthalmic surgical laser system which can be adapted for use with the present invention to provide for precisely controlling and determining the location of the interaction point of a surgical laser beam, and for controlling the shape of the cornea during ophthalmic surgery, is set forth in co-pending U.S. patent application Ser. No. 07/967/253, entitled "METHOD AND APPARATUS FOR OPHTHALMIC SURGERY" and assigned to the assignee of the present invention. In that embodiment, a transparent applanator plate is placed in contact with the cornea of a patient's eye. The applanator plate creates a fixed positional frame of reference from which a laser beam control system can determine the desired point or points of which to focus the surgical laser beam, and thereby direct an interaction point of the beam to a very precisely defined locations within the patient's eye. The surface of the applanator plate in contact with the patient's eye can be planar, concave, or convex, with either a spheric or aspheric curvature, a compound curve, or any other shape chosen by the surgeon. Applying the applanator plate to the cornea of the patient's eye causes the cornea to conform to the shape of the applanator plate.

Figure 14A:
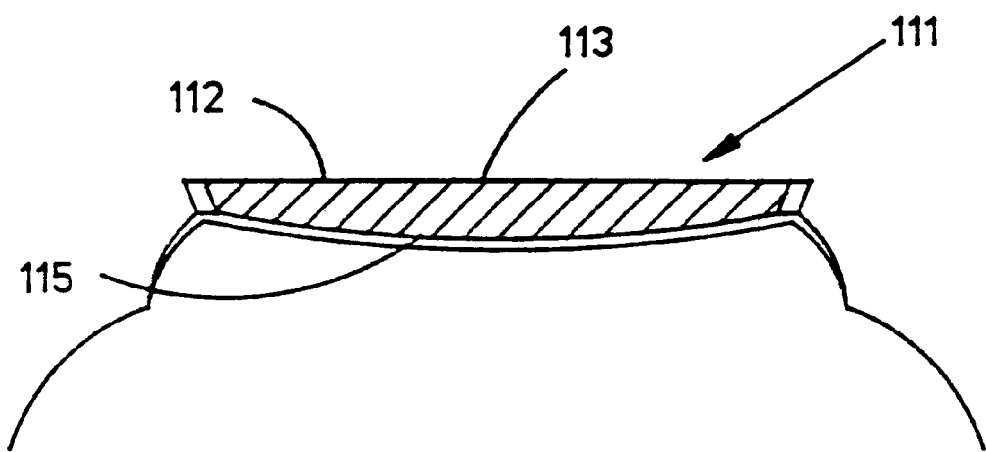
FIG. 14A is a cross-sectional side view of a convex applanator plate applied to an eye.
Figure 14B:
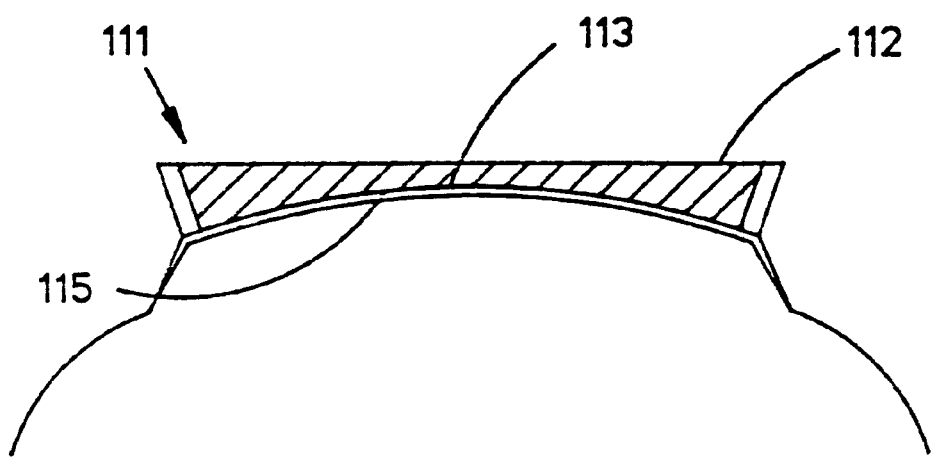
FIG. 14B is a cross-sectional side view of a concave applanator plate applied to an eye.

For example, FIG. 14A shows a cross-sectional side view of a convex applanator plate 111. The applanator plate 111 has at least two surfaces, a tip surface 112 and a corneal surface 113. The applanator plate 111 is placed in contact with the corneal epithelium 115 and deforms the cornea to conform to the convex shape of the corneal surface 113. As another example, FIG. 14B shows a cross-sectional side view of a concave applanator plate 111 applied to an eye. The applanator plate 111 is placed in contact with the corneal epithelium 115 and deforms the cornea to conform to the concave shape of the corneal surface 113.

A surgical tip at the distal end of an articulated arm having flexible joints is placed in contact with the tip surface 112 of the applanator plate 111 and follows any motion of the patient's eye. The articulated arm is coupled to a surgical laser source including a laser beam control system, such as the system described in co-pending patent applications filed by the present inventor for inventions entitled "Two Dimensional Scanner-Amplifier Laser" ( U.S. patent application Ser. No. 07/740/004), and "Method of and Apparatus for, Surgery of the Cornea" (U.S. application Ser. No. 07/788, 424). The surgical laser source also includes the source of the laser beam. The articulated arm directs the laser beam to the surgical tip, translating the motion of the beam relative to a reference frame fixed to the surgical laser source to a reference frame fixed with respect to the applanator plate to which the surgical tip is in contact. Since the shape of the cornea conforms to the contour of corneal surface 113 of the applanator plate 111, incisions of various shapes can be made by selecting an appropriate applanator plate and controlling the surgical beam to move linearly with respect to the fixed frame by the applanator plate.

The applanator plate 111 also provides a means to control the contour of the index of refraction boundary between the corneal epithelium 115 of the patient's eye and the air. Controlling the contour of this boundary reduces the distortion of the surgical laser beam which would otherwise be present due to the curvature of the outer surface of the epithelium and the difference in the index of refraction between the air and the stroma underlying the epithelium. The index of refraction of the applanator plate is preferably closely matched to the index of refraction of the cornea (i.e., index of approximately 1.38). The tip surface 112 of the applanator plate 111 is selectively shaped to provide a desirable contour at the boundary between the index of refraction of the stroma and air.

Thus, the applanator plate 111 serves at least three purposes: (1) to provide a positional reference for a surgical laser; (2) to control the shape of the patient's cornea during a surgical laser procedure; and (3) to provide a boundary between the epithelium and air, the contour of which can be controlled to reduce the distortion of the surgical laser beam. When used with the present invention, the applanator plate allows precise control of tissue removal.

Figure 15A:
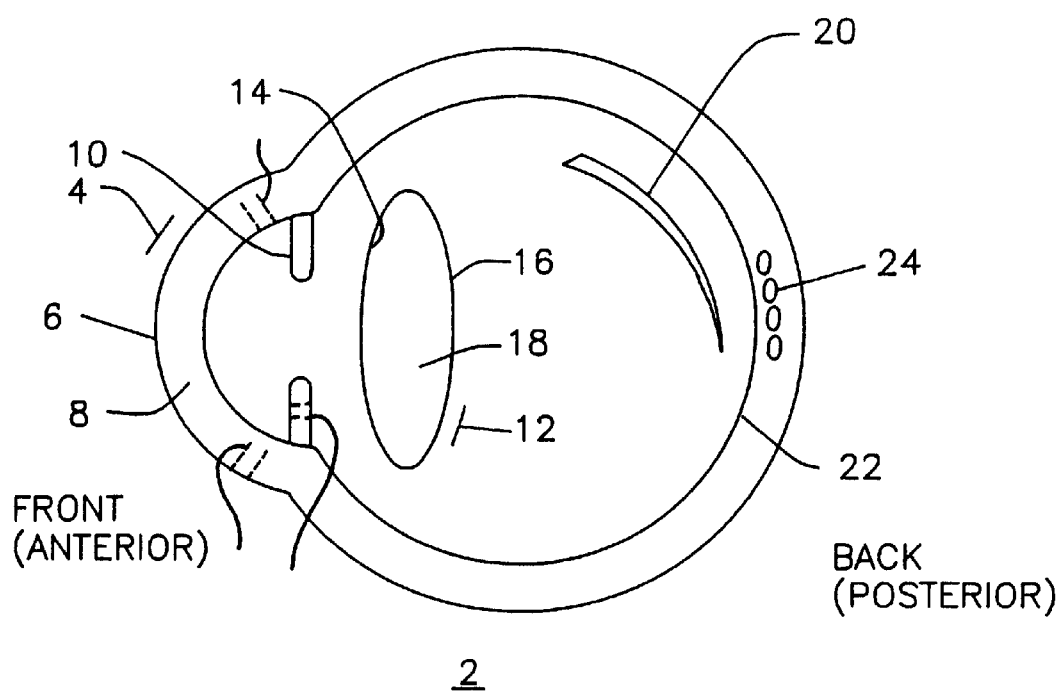
FIG. 15A is a schematic of the eye, showing general reference points, including cornea, iris, lens, and retina.

FIG. 15A demonstrates some of the eye's 2 generally designated landmarks. Most anterior is the cornea 4, whose curved anterior surface 6 and inner stromal substance 8 are shown. Posterior to cornea 4 is iris diaphragm 10. Behind irs 10 is lens 12, whose anterior capsule 14, posterior capsule 16 and internal substance 18 are shown. Also shown is vitreous membrane 20, retinia 22, and an example of sub-retinal pathology 24.

Figure 15B:
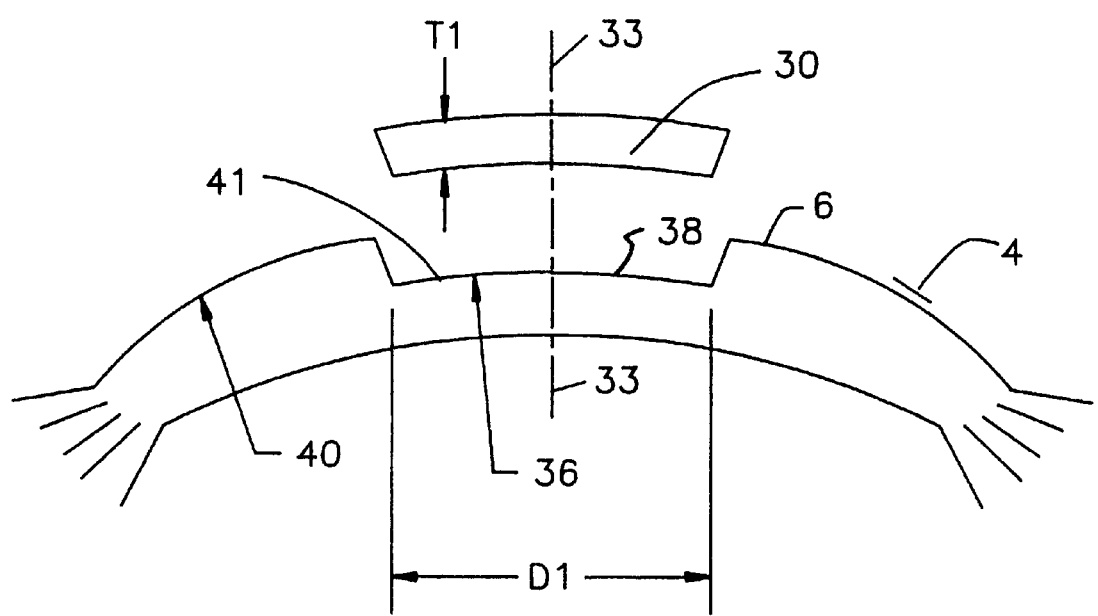
FIG. 15B is an elevation in section, through a plane intersecting and parallel to the visual axis, demonstrating a lamellar keratectomy of parallel faces.

FIG. 15B demonstrates the principle of a lamellar keratectomy. In this generic drawing, the keratectomy may have been produced by a mechanical microkeratome or by a laser. In this procedure a circular (in front view) section of tissue called a lamellar disc 30 is removed from the front of cornea 4 Disc 30 is of constant thickness T1 and of diameter D1. The keratectomy is centered upon the visual axis 33 of the patient's cornea 4. Because disc 30 is of constant thickness, the radius of curvature 36 of the keractectomized bed 38 is equal to the initial radius of curvature 40 of cornea 4 minus T1, and surface 41 of bed 38 is thus concentric to anterior corneal surface 6.

Figure 15C:
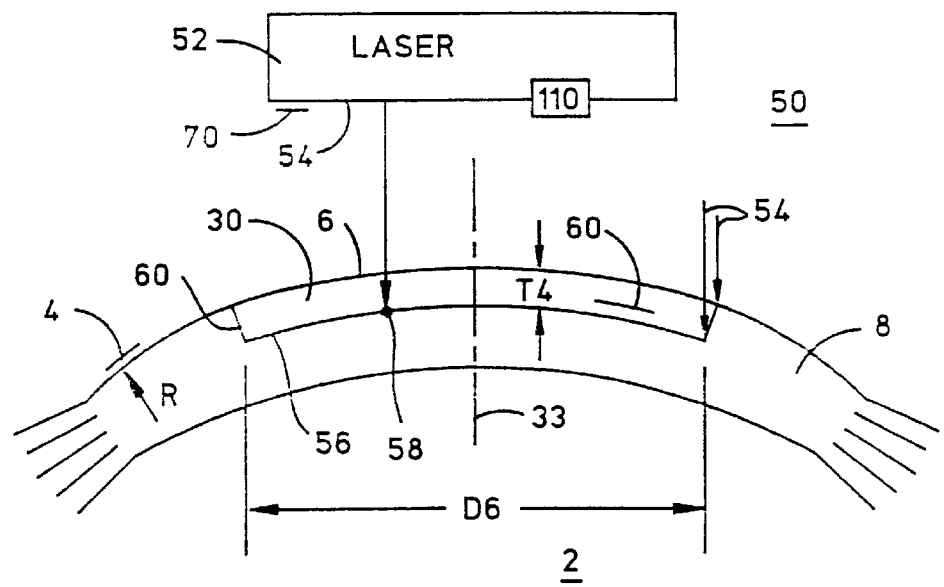
FIG. 15C is an elevation in section of the cornea demonstrating the principle of the laser microkeratome in which laser radiation is used to perform a lamellar keratectomy.

FIG. 15C demonstrates the principle of the laser microkeratome, generally designated 50, used to produce a lamellar photokeratectomy. The procedure is carried out by photodisruption with a laser 52 using a wavelength of radiation that is transmissive by the cornea 4. Internal corneal substance 8 is exposed to focussed laser radiation 54 over diameter D6, typically centered across the visual axis 33, of the eye 2. The laser energy is delivered across area of ablation 56 of diameter D6, which is circular in a frontal elevation and forms a line 56 appearing as an arc in the sectioned elevation which is FIG. 15C. The energy is delivered by focussing the laser beam 54 into a small laser spot 58, whose diameter can be selected. The spot is focussed at a level beneath corneal surface 6 equal to T4, the depth of the resection. Spot 58 is then moved in a scanning motion under computer control, along the line 56, which in fact represents the area of ablation of diameter D6. The spot size is chosen to minimize adjacent tissue damage, as is the irradiance of the laser beam itself. The laser beam is fired in a series of pulses, each pulse having a duration which we define as its pulse width. In the preferred embodiment, these pulse widths are ultrashort, preferably in the range of 10–400 femtoseconds to achieve a power density at the focal point 58 that will allow photodisruption to take place while keeping the beam energy or irradiance to a minimum. The energy level will vary depending on the spot size, wavelength and pulse width chosen. It is important to keep the energy level of the laser to a minimum, as the surface quality produced will become rougher as the energy is increased.

The scanning of the spot can be carried out in a number of ways, depending on the design of the laser. For example, concentric circles, increasing or decreasing spirals, linear scanning while varying the length of each line to allow a circular pattern, etc. have been used with success. After scanning the area 56, which is a curved surface whose radius of curvature=R—T4, the delivery system may be programmed to ablate one or more additional concentric and adjacent surfaces 60 (shown only in part as an arc), moving from posterior to anterior, to ensure complete separation of the anterior cap 30 from the bed 38 (FIG. 15B), defined by area of ablation 56 (FIG. 15C). Following ablation at depth T4, the laser spot is then scanned outward in a circular fashion beginning at depth T4, or at a slightly greater depth to ensure transection through surface 60, and ultimately scanned forward or outwardly until the scanned spot passes through the anterior corneal surface 6. When sectioning along line 60, which may be a plane or part of a wall of a cylinder or cone, depending on the geometry or shape of the peripheral bevel or flange 60, the spot is typically scanned in either a continual spiral pattern or as a series of concentric circles, of the same or progressively increasing diameter. The exact pattern and energy levels may be altered as one ablates the vertical or sloping edge 60 of the disc 30 to ensure satisfactory ablation of the varying tissue materials. At this point the lamellar photokeratectomy has been completed. Its diameter is D6, it is of constant thickness T4, and it has a vertical edge, or, if desired, a sloping edge 60 of any desired angle. This keratectomy may be then left as is, or the lamellar disc can be grasped and removed by the surgeon in anticipation of further surgery on the disc 30 or the ablated bed 38. The lamellar disc is of a thickness that is less than the thickness of the cornea, and may therefore be called a partial thickness lamellar disc.

Figure 15D:
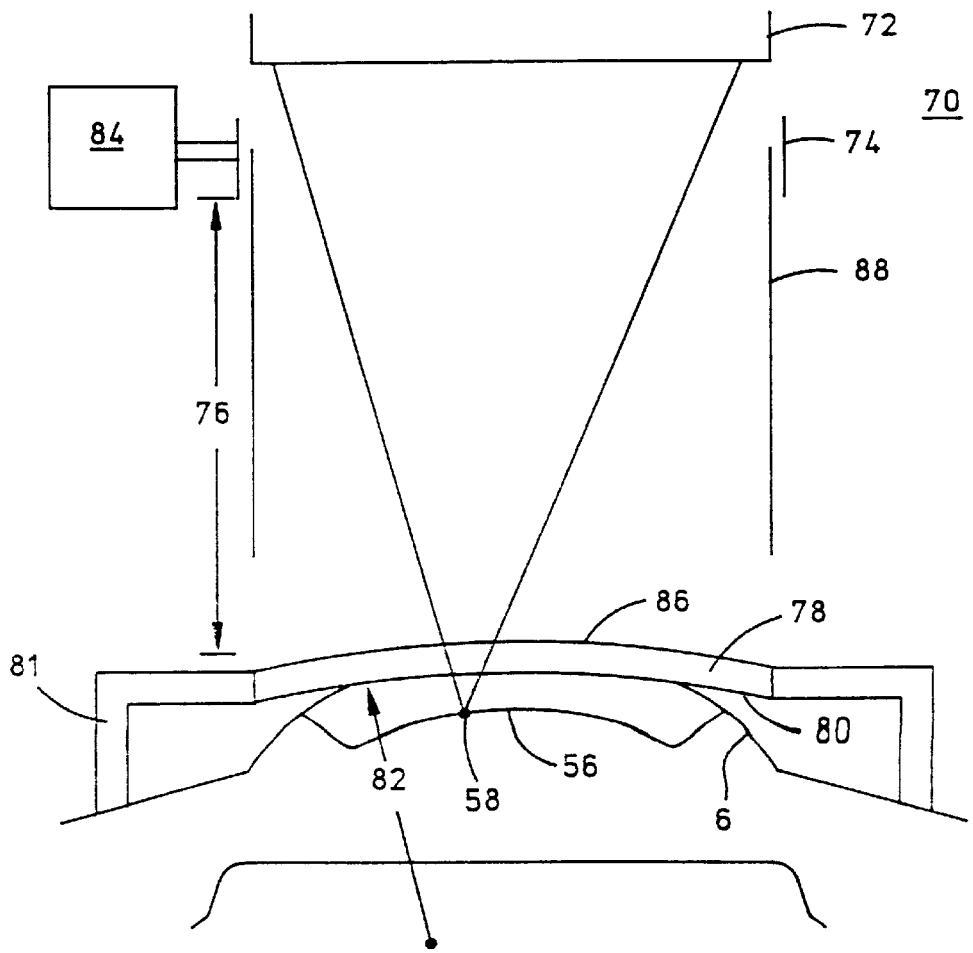
FIG. 15D is an elevation in section of the cornea demonstrating the principle of the laser microkeratome.

As a means of locating the area of ablation a preferred embodiment is shown in FIG. 15D. A laser delivery system, generally designated 70, comprising the laser 72 and means for scanning 74 laser spot 58 in three dimensions, is physically coupled at a predetermined distance 76 to contact lens 78 which is transparent to the laser energy being delivered.

The contact lens 78 comprises a curved surface 80 whose radius of curvature 82, approximately 8–12 mm, is somewhat greater than the typical radius of curvature of the cornea R (see FIG. 15C) to be operated upon, typically 7.7–8.2 mm. The index of refraction of the contact lens 78 is approximately that of the cornea, 1.376. Also, the contact lens may come with a completely flat surface 80. This has certain advantages when performing intrastromal cavitation and lamellar keratectomy, as the laser need only scan in two dimensions in order to remove a lamellar disc of parallel faces. It also may simplify the distortion produced in the cornea from the plasma bubbles formed.

As shown in FIG. 15D, during the operation the curved surface 80 of the contact lens 78 is abutted to provide full contact with the anterior corneal surface 6, thus locating the intended area of ablation 56 at a known position with respect to the laser delivery system 70. (This may be accomplished or assisted by a peripheral corneal suction ring 81, as is well known in keratomileusis surgery. In this case, displacement movement of the contact lens within the ring in the x—y direction can be allowed by overlapping plates. This is important, as it allows the surgeon to center the applanation plate (if flat surface used) or contact lens surface on the visual axis of the patient so laser ablation is carried out with centration around the visual axis). The contact lens may, however, be simply placed against the cornea by slight pressure, or with assistance of a lubricant adhesive. This allows the laser spot 58 to be precisely located on intended area of ablation 56 and scanned across the entire area under computer 84 control. The upper surface 86 of the contact lens 78 may be flat to eliminate refraction of the laser beam 88, although any shape is possible and many shapes can be optically accounted for in the computer program.

FIG. 15C can also be used to describe a variant of the lamellar photokeratectomy using the laser microkeratome described in FIGS. 15C and 15D. This lamellar keratectomy procedure is performed to correct hyperopia. In the present invention, a laser microkeratome is used rather than mechanical means. In this instance, the same 72, delivery system 74, and contact lens 78 are used. The energy considerations and scanning will not be repeated in detail. The principle of the operation is to vary the diameter D6 or the thickness T4 (FIG. 15C of the resected lamellar disc 30. The principle of the operation is such that a controlled ectasia or forward bowing of the cornea results when a deep (70–90% of corneal thickness) lamellar disc 30 of small diameter, typically 5.5–7 mm, is resected and simply replaced, due to the pressure exerted from the intraocular fluid. This forward bowing causes a steepening of the central cornea. Diameter D6 and thickness T4 can be varied to achieve a range of curvature modifications, which may include those for correction of accompanying astigmatism, regular or irregular. Thickness T4 may be uniform or non-uniform across the area of ablation.

Figure 15E:
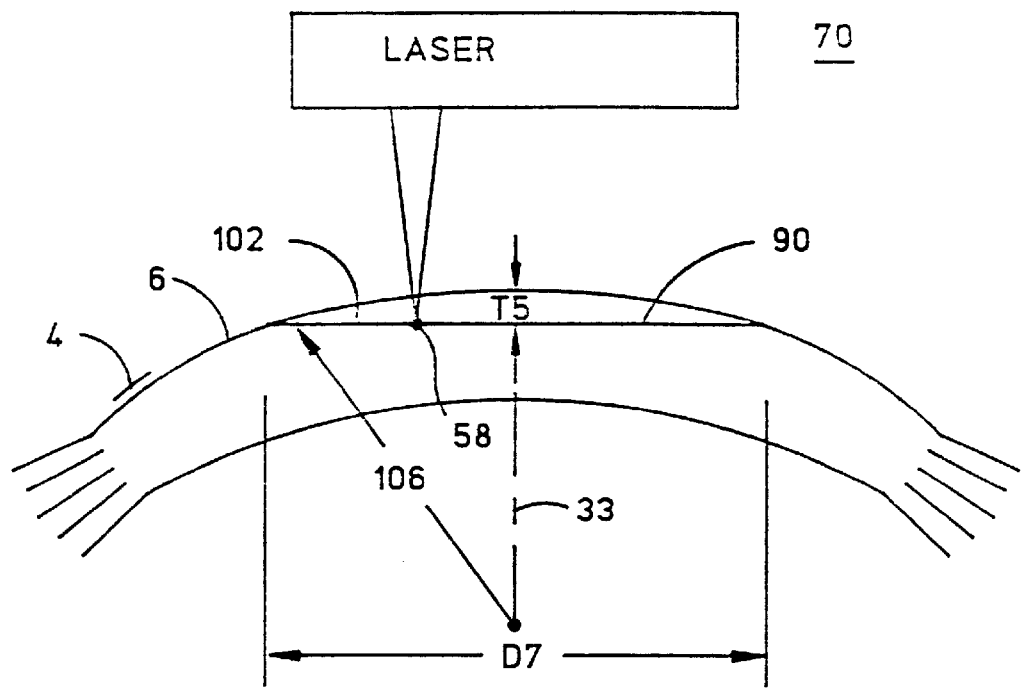
FIG. 15E is an elevation in section demonstrating the production of a new, flatter corneal surface using the laser microkeratome.

FIG. 15E demonstrates another variant of lamellar photokeratectomy using the laser microkeratome described in FIG. 15D. In this instance, the same laser 72, delivery system 74, and contact lens 78 are used. The energy considerations and scanning will not be repeated in detail. The purpose of the operation described in FIG. 15E is to create directly a new anterior surface 90 for the patient's cornea 4. The new surface 90 is designed to have a new curvature such that following its creation the patient's eye will now focus light in a new way. In FIG. 15E, this surface is shown as a flatter surface designed to correct myopia, but it may also be a steeper surface to correct hyperopia, or an astigmatic surface to correct astigmatism. It may also be aspheric to correct irregular astigmatism or alter spherical aberration or improve the optical functioning of the ablated cornea. In FIG. 15E, the computerized scanning delivery system 70 scans the spot 58 through the cornea 4 of the patient as in FIG. 15D except that in this case the depth of the spot 58 below the anterior corneal surface 6 varies as prescribed to create the curved surface 90 desired. Scanning typically begins at the visual axis 33 and proceeds therefrom. Energy adjustments and minor alterations in the geometry at the edge of the disc may be necessary to fully and cleanly delimit the upper lenticule (which in FIG. 15E is seen to be a lens with convergent refractive power).

In FIG. 15E this ablation 90 is deepest at the visual axis 33 and tapers to meet corneal surface 6, or close to it, at diameter D7. The maximal depth of the ablation is T5. The optic zone diameter is D7, and the refractive power of this new surface is calculated from standard formulae using its radius of curvature (calculated beforehand from the patient's refractive error, curvature, etc.), and the indices of refraction of air and corneal tissue. Following the ablation, the surgeon lifts off upper lenticule 102 which has been freed by ablation to reveal the new surface.

Figure 15F:
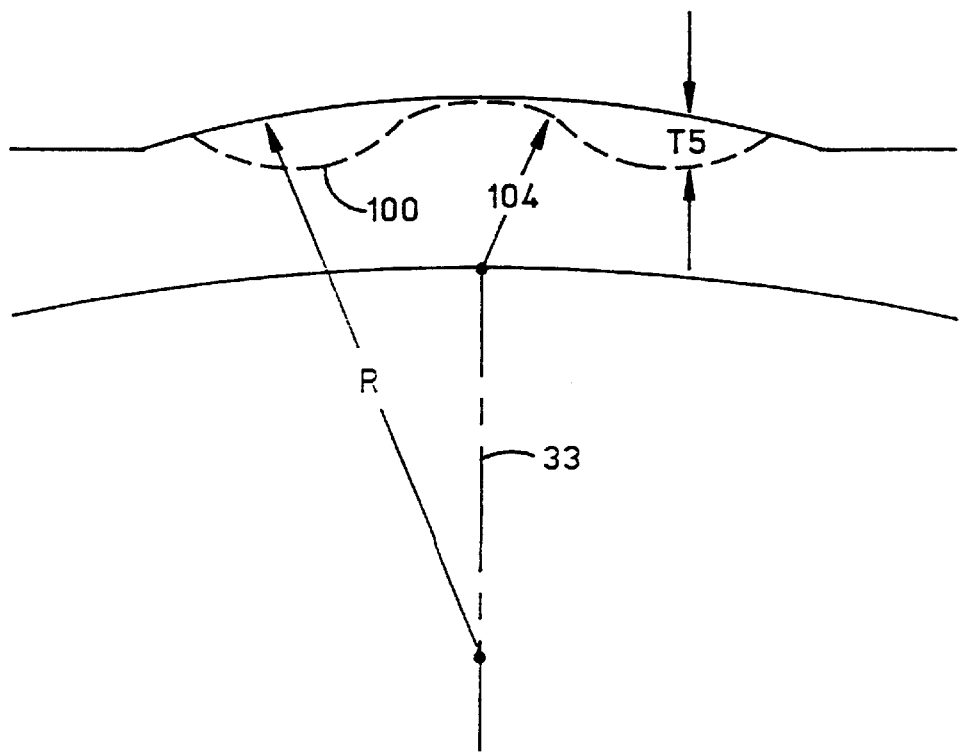
FIG. 15F is an elevation in section demonstrating the production of a new, steeper corneal surface, using the laser microkeratome.

FIG. 15F shows an area of ablation 100 whose central radius of curvature 104 is less than the radius of anterior corneal curvature R and which corrects hyperopia or far-sightedness.

For correction of astigmatism, a toric surface is produced with a major and minor radius of curvature, one of which 106 is shown in FIG. 15E.

FIG. 15C also represents another embodiment of the invention. In this case, laser beam 54 is not referenced, or directly coupled physically, to the anterior corneal surface 6 by contact in order to localize the exact position of laser beam spot 58 with respect to the cornea 4. Instead, a scanning delivery system 70 is used in conjunction with a tracking system 110. Such delivery systems, including scanning and tracking systems that can precisely locate the laser spot 58 within the cornea 4, are already in use. Such laser corneal systems have been described in commercial literature by Intelligent Surgical Lasers, Inc., of San Diego, and Phoenix Laser Systems, of San Francisco. They have also been described in U.S. Pat. Nos. 4,848,340, Billie and Brown, issued Jul. 18, 1989, 4,901,718, Billie and Brown, issued Feb. 20, 1990, and 5,098,426, Sklar et al., issued Mar. 24, 1992. Using such a system, the computer program directs the laser beam spot to be scanned through the corneal tissue in the same patterns and for the same purposes as described above for the contact lens 78 type of delivery system.

Figure 15G:
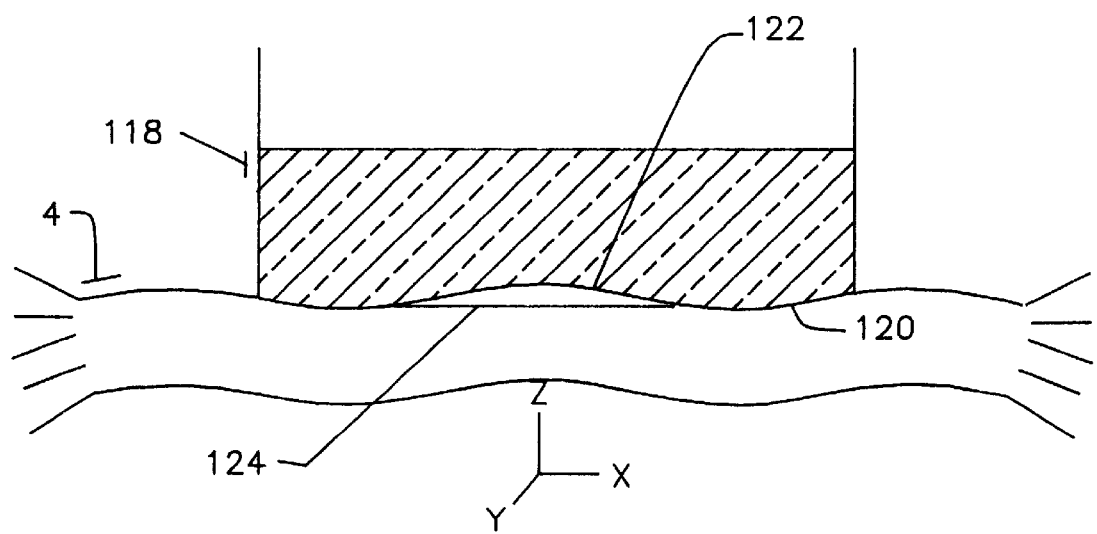
FIG. 15G is an elevation in section demonstrating the production of a new corneal surface using a deforming lens to allow ablation in two dimensions.

FIG. 15G describes another embodiment of the invention. In FIG. 15E laser beam spot 58 scans a curved surface in order to create a new corneal surface 90. This necessitates tracking in three dimensions. However, if the contact lens delivery system is provided with a range of contact lenses, insertable into the base of the delivery system, or a fixed part of it, then the cornea 4 will be deformed into a new desired shape during laser ablation. In FIG. 15G this contact lens 118 is such that the peripheral cornea is depressed more than the central cornea 122. Laser ablation is carried out in only two dimensions, as the three dimensional surface to be scanned in FIG. 15E has now been reduced to a two-dimensional surface 124, for practical purposes. Thus, by using only X—Y scanning, the Z axis tracking can be eliminated, which is a simplification. The contact lenses that are part of the delivery system can be spherical, aspheric, toric, or any shape desired. The contact lens in FIG. 15G provides for correction of myopia, as the postoperative cornea will be flatter. The shape of lenses for hyperopic and astigmatic lenses will not be shown, as these are easily derived.

Figure 15H:
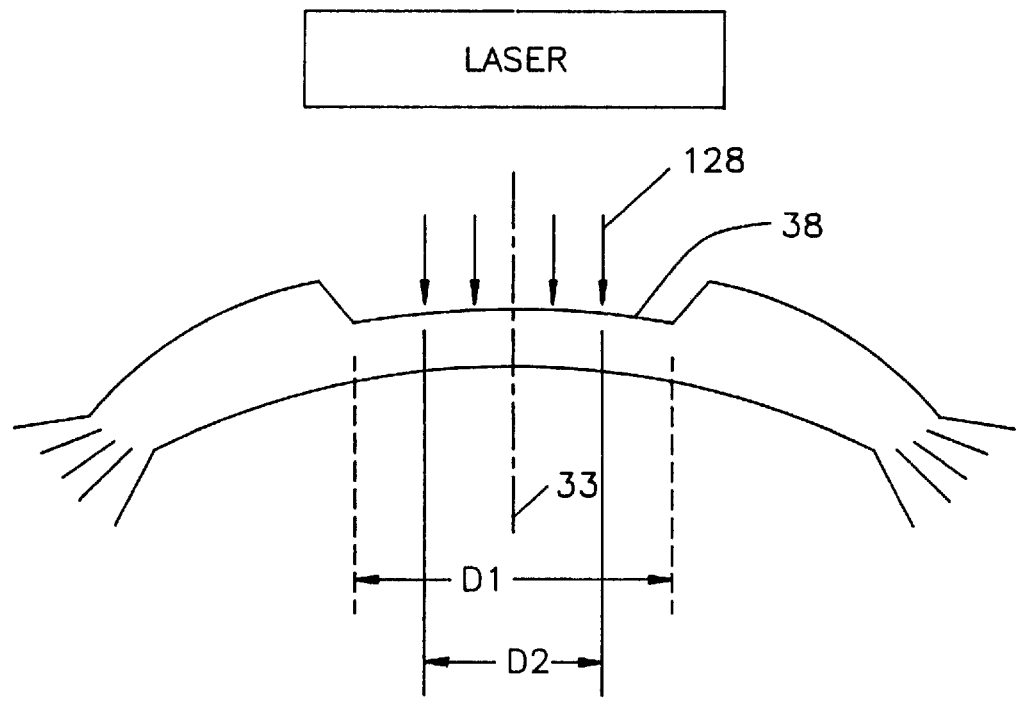
FIG. 15H is an elevation in section of the cornea demonstrating laser keratomileusis-in-situ, whereby laser radiation is applied to the stromal bed following a lamellar keratectomy.

FIG. 15H demonstrates the operation of laser keratomileusis-in-situ. Here the keratectomized bed 38 as produced in FIG. 15B is irradiated with a laser source to ablate the stromal tissue of the bed 38. The laser source may be any laser capable of ablating corneal stroma, whether by photoablative decomposition, by photodisruption or by photovaporization, and using wavelengths from any part of the electromagnetic spectrum. For example, an ultraviolet laser such as any commercially available excimer laser could be used to carry out photoablative decomposition, a transmissible wavelength laser such as a Ti:Sapphire or Nd:YLF could be used for photodisruption and a holmium, HF, or Er:YAG could be used for photovaporization. Examples of lasers are for illustration, and any suitable laser could be used. In addition, the laser source can be pulsed, and its pulse duration can be short or ultra-short in pulse width.

The laser radiation is distributed onto the central area of bed 38, is typically circular in frontal elevation and is of diameter D2, which is less than D1. D2 is typically 3–5 mm in diameter, whereas D1 is typically 6–8 mm. The irradiation is carried out via aperture or wide beam 128 control mechanism or can be via a scanned spot of very small diameter and guided by a laser's computer control system. The energy distribution of the laser beam 128 is constant over diameter D2 such that the keratectomy produced is of constant depth across D2. In addition, there are several variants as to how this resection may be done.

Using ultraviolet photoablative decomposition or infrared photovaporization, the tissue would be gradually ablated away until the end point is reached. With photodisruption the tissue can be ablated away similarly from front to back or the keratectomy can be performed as described elsewhere in this document under the laser microkeratome.

Figure 15I:
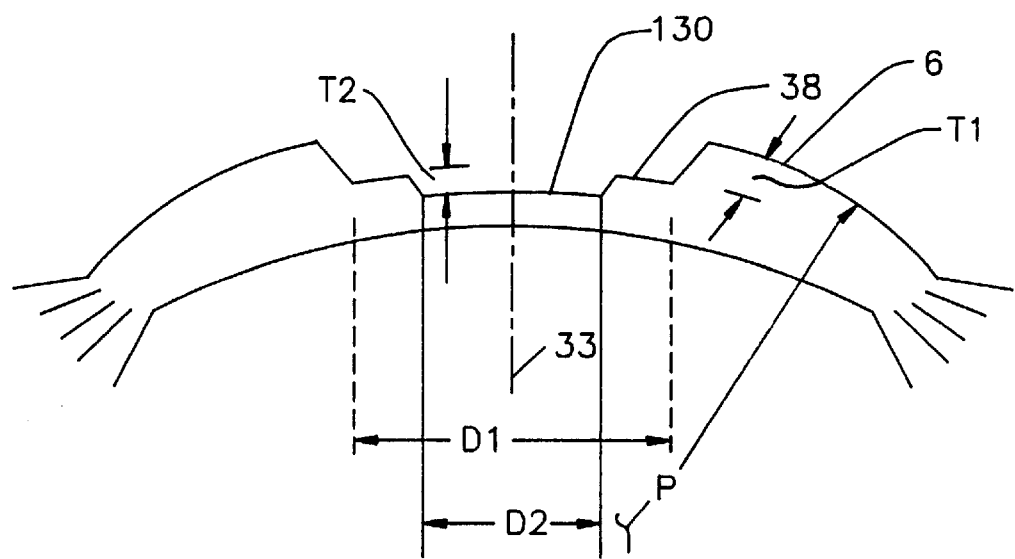
FIG. 15I demonstrates as an elevation in section the keratectomy of constant depth produced in FIG. 15H.

FIG. 15I shows the keratomileusis in-situ procedure at the stage after completion of the second keratectomy, which is on the bed following the first keratectomy of diameter D1 and thickness T1. This second or optical cut creates a cavity of constant depth T2, and with diameter D2. The radius of this second bed 130 is given as equal to R−(T1+T2) and this bed is concentric with both the anterior corneal surface 6 and the bed 38. It is centered on visual axis 33. T2 is typically in the range of 20–200 microns, but can be otherwise.

Figure 15J:
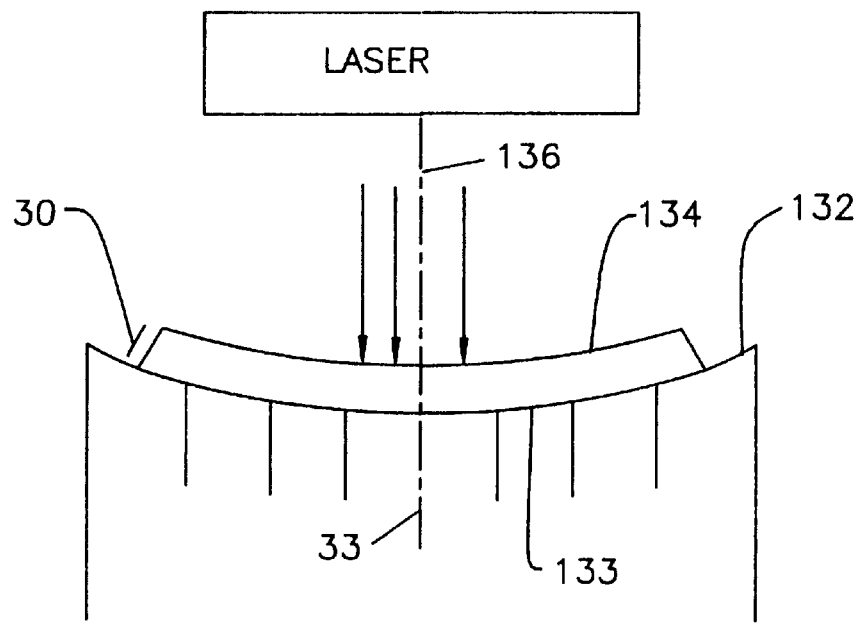
FIG. 15J demonstrates as an elevation in section a resected lamellar disc on a block which is being treated with the laser on its stromal surface.

FIG. 15J demonstrates a second way of performing keratomileusis-in-situ, whereby the optical or refractive cut is made onto the back stromal surface of the first keratectomized disc rather than onto the corneal bed 38. In this instance, following the initial keratectomy on the patient or donor cornea, the resected disc 30 of diameter D1 and thickness T1 is inverted and placed atop a concavity 132 of curvature 133 similar to the human cornea, though this is not necessary. The disc 30 may be placed into a closed chamber to keep humidity within and which is transparent to the wavelength of the laser used. The posterior stromal surface of this disc is then exposed to the laser radiation 136 as described under FIG. 15H, exposing an area of diameter D2 and removing a parallel faced lamella of tissue of thickness T2. The ablation is carried out with the center of ablation corresponding to the visual axis 33 of the patient, which has been previously identified and marked as in radial keratotomy surgery.

Figure 15K:
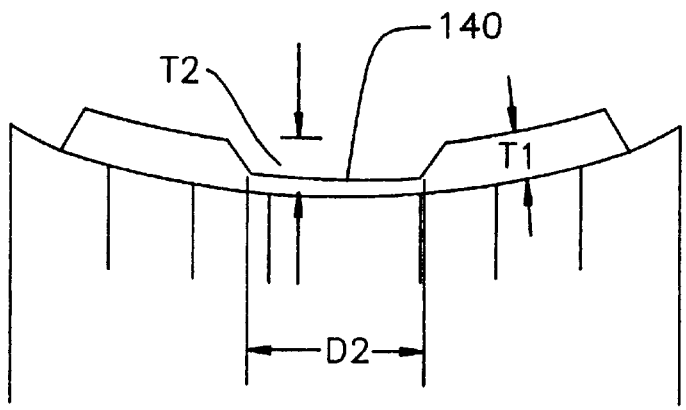
FIG. 15K demonstrates as an elevation in section the lamellar disc of FIG. 15J following treatment whereby a circular cavity of constant depth has been produced.

FIG. 15K shows the completion of the process described in FIG. 15J. Here the parallel-faced optical cut 140 has been completed. A circular section of cornea of constant thickness T2 and diameter D2 has been removed from the posterior aspect of disc 30.

Figure 15L:
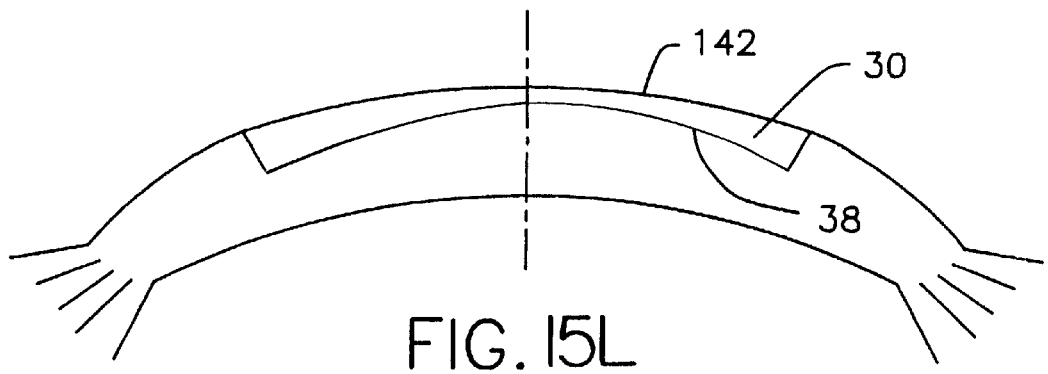
FIG. 15L is an elevation in section of a cornea following laser keratomileusis-in-situ demonstrating the repositioning of the disc and flattening of the central cornea.

FIG. 15L demonstrates the completion of the keratomileusis in-situ procedure. Here the disc 30 has been replaced on bed 38. Because a cavity has been removed from either the disc 30 or from initial bed 38, the cavity in either case will collapse and the posterior aspect of disc 30 will come into contact with either bed 38 or 134, depending upon whether the optical resection was performed on the disc 30 or the bed 38. Because of this collapse, the anterior curvature of the cornea will be altered to a new curvature 142 designed to correct the optical error of the patient. In this case the cornea is flattened and myopia is corrected.

Figure 15M:
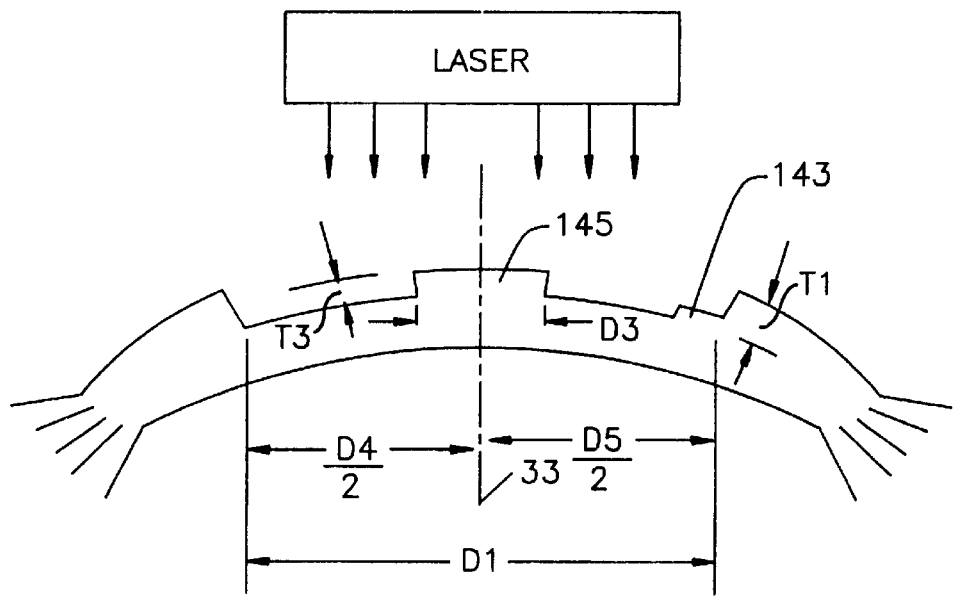
FIG. 15M is an elevation in section demonstrating keratomileusis-in-situ, with ablation of the bed, for the correction of hyperopia.

FIG. 15M demonstrates the keratomileusis-in-situ procedure for hyperopia, or farsightedness. As in FIG. 15B, a lamellar keratectomy is performed on the patient or donor eye using either a mechanical or a laser microkeratome. This removes, as in FIG. 15B, a disc 30 of thickness T1 and diameter D1. As in FIGS. 15H–I, the bed of the patient is exposed to laser radiation by the methods described. In this case, however, the distribution of energy is different. Here laser energy is applied to ablate to a constant depth, but in this case there is no ablation in the immediate central area, centered on visual axis 33. The diameter of the non-ablated projection 145, which is typically circular in frontal elevation, is given as D3. Thus the ablated area is seen to be a ring of ablation, concentric with visual axis 33, and whose width can vary from (D4–D3)/2 to (D5–D3)/2, depending on whether a blending flange or peripheral wing 143 of blending is included to make for a smooth postoperative fit. The depth of the annular ablation is constant over the area ablated, and is given as T3. The height T3 and width D3 of the projection can vary to produce a range of desired optical effects. For example, the greater T3 is, the greater the amount of secondary curvature induced and the greater the amount of hyperopia corrected. Similarly, the correction will also be dependent on the width of the annular ablation, which can also be varied as desired.

Figure 15N:
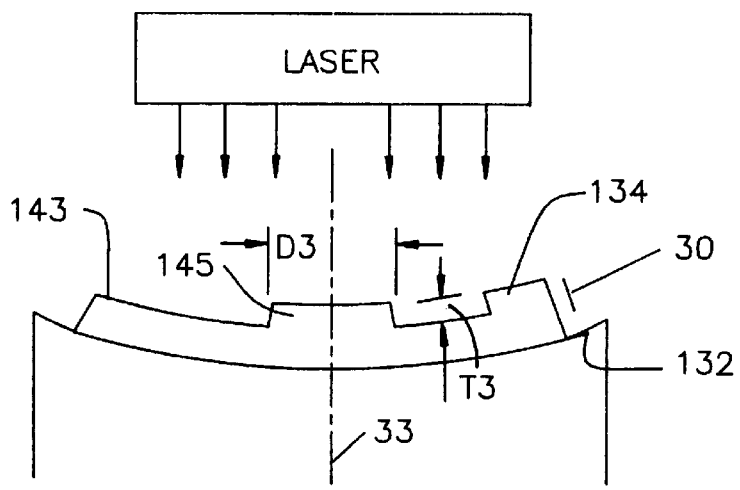
FIG. 15N is an elevation in section demonstrating keratomileusis-in-situ, with ablation of the disc, for correction of hyperopia.

FIG. 15N demonstrates hyperopic correction by ablating disc 30. The lamellar disc 30 has been placed in a concavity 132 with radius of curvature similar to the human cornea and laser irradiation is applied to its upper stromal surface 134. The anterior aspect is placed down against the holding block 132. The stromal surface is then exposed as in FIG. 15N such that an annular circular ablation is effected sparing a circular central projection. The central projection has diameter D3 and is T3 in height. Varying height T3 of the projection and the width of the annular ablated zone will allow the surgeon to induce varying optical change in the patient's refractive error.

Figure 15O:
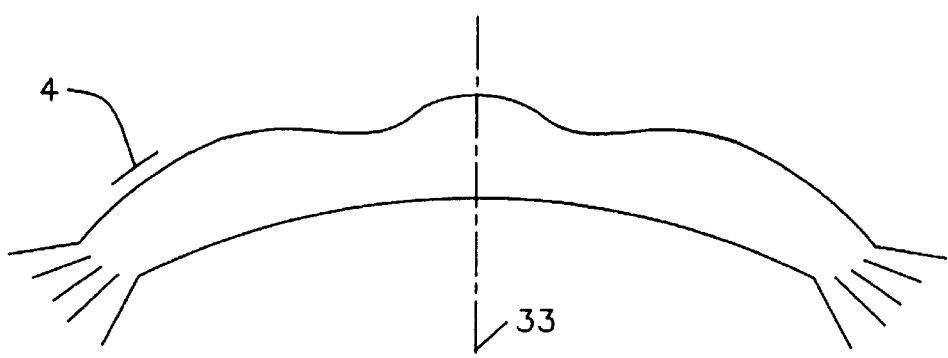
FIG. 15O shows the reconstructed and steepened cornea following laser keratomileusis-in-situ for hyperopia.

FIG. 15O demonstrates the final appearance of the patient's cornea after replacement of the keratectomized disc in hyperopic correction. Because of the central cylindrical protrusion, whether on the keratectomized disc 30 or on the bed 38, the central cornea of the patient is steepened and hyperopia corrected after placement of the disc because the annular cavity ablated collapses and falls posteriorly, while the central apex at the visual axis 33 is prevented from doing so by the cylindrical protrusion.

Figure 15P:
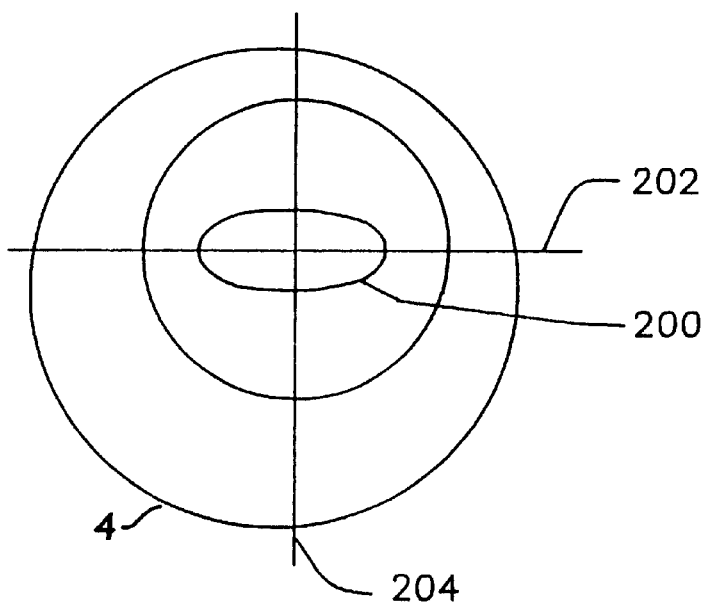
FIG. 15P is a frontal view demonstrating the correction of astigmatism by laser keratomileusis-in-situ.

FIG. 15P demonstrates in frontal section of cornea 4 the correction of astigmatism with this technique, with or without accompanying myopia or hyperopia. To correct astigmatism, the first keratectomy is performed in the usual manner. Then the bed, or keratectomized disc, is ablated as previously described. However, in this case, the ablated cavity 200 has an elliptical outline. The orientation of the ellipse with respect to major 202 and minor 204 axes of astigmatism is critical. In describing astigmatism, there is a meridian of the eye with maximal optical refractive power and another, usually orthogonal, meridian with minimal refractive power, with the corneal astigmatism defined as the difference in corneal power of these two meridians. Thus, to eliminate astigmatism, the axis or meridian of greatest corneal power, here shown as 202, is aligned along the major axis of the ellipse, as greatest correction or reduction of corneal power takes place along the major axis. The reason is that the disc, when conforming to the ablation cavity will have greater opportunity to fall into the trough as the width of the ablation increases. The axes are marked before laser application, as typically done, and the laser irradiation appropriately delivered by the laser with diaphragm, ablatable mask, or scanning spot delivery system to create the elliptical ablation. For combined myopia and astigmatism, the dimensions of the major and minor axes of the ellipse and the depth of the ablation are calculated on the basis of the refractive error to be corrected.

Figure 15Q:
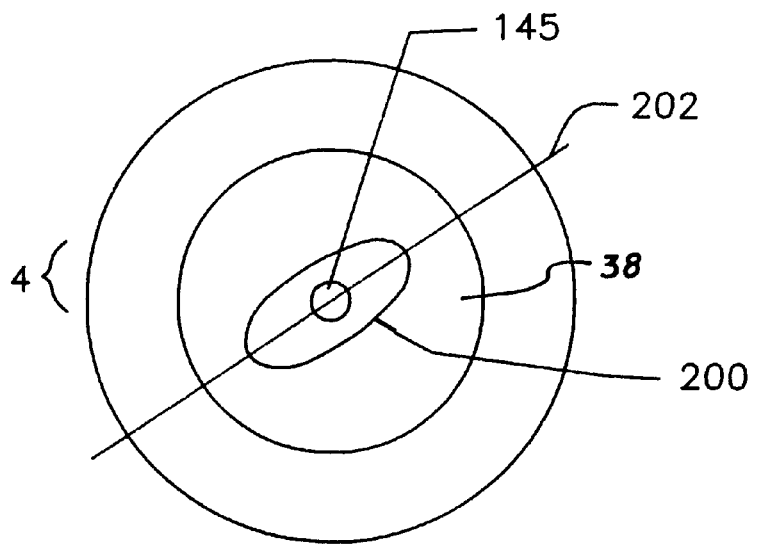
FIG. 15Q demonstrates, in frontal view, the correction of combined hyperopia and astigmatism.

FIG. 15Q demonstrates the corresponding case for correction of hyperopia and astigmatism. In this case the cornea 4 undergoes a keratectomy exposing the bed. The laser energy is applied to leave a central projection, as in hyperopia correction, but surrounded by an elliptical ablated zone. The major and minor axes of the ellipse, and the height T3 and width D3 of the central projection 145 are calculated from the components of the patient's refractive error.

Figure 15R:
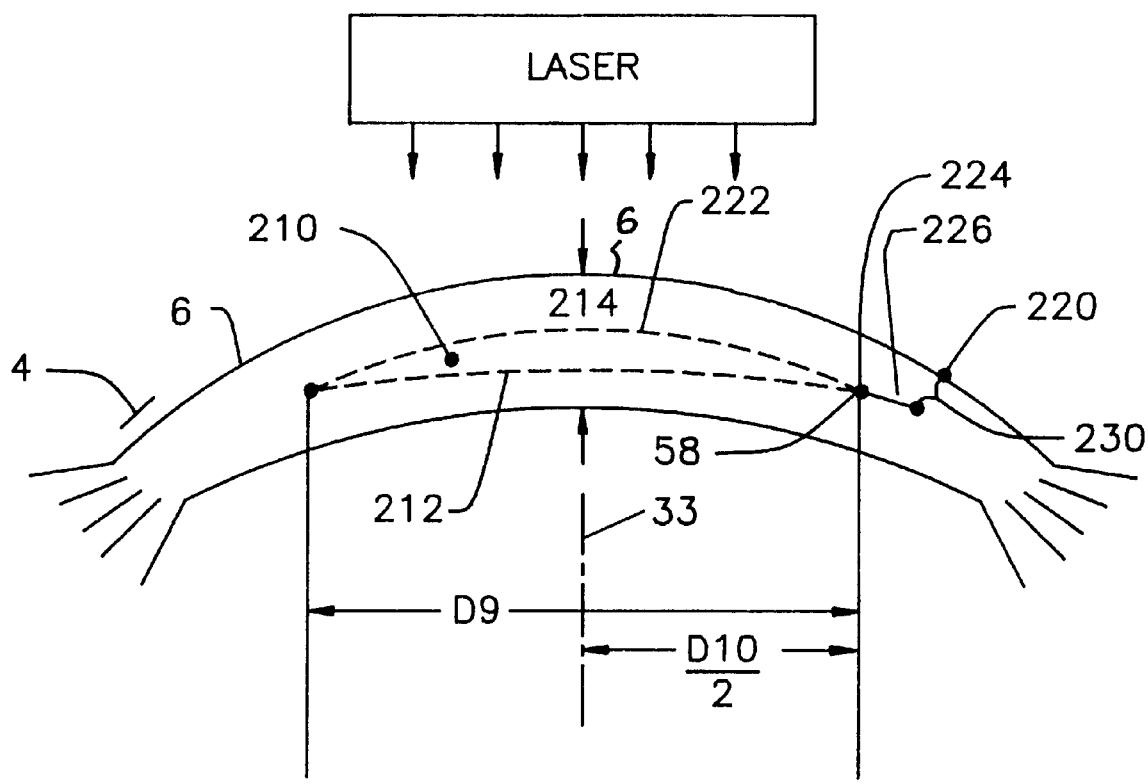
FIG. 15R is an elevation in section of the cornea demonstrating laser production of an intrastromal cavity designed for myopic correction along with an extension that allows for relaxation of Bowman's membrane.
Figure 15S:
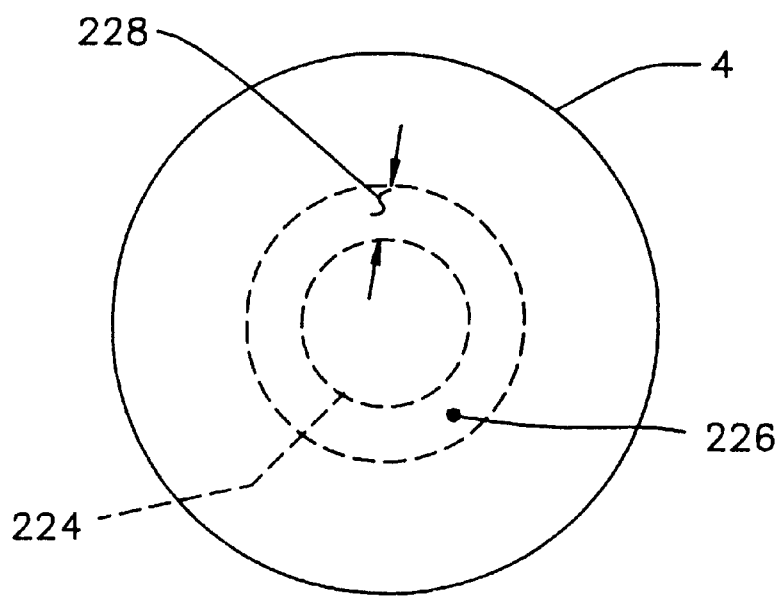
FIG. 15S is a frontal view of FIG. 15R demonstrating the circular optic zone of the cavity produced and the larger diameter relaxation incision.

FIGS. 15R–S demonstrate the operation of corneal intrastromal cavitation for the correction of refractive errors. The principle is to ablate or destroy a volumetric portion of tissue 210 from within the cornea 4 of such calculated shape such that once the optical breakdown products have been absorbed, the anterior corneal surface 6 is displaced posteriorly to close the potential space formed. This results in a new, desired anterior curvature calculated to eliminate the patient's problem. The shape of the volume 210 to be ablated is obviously related to the desired change in anterior curvature and the calculations for this type of procedure are well known.

The process for the correction of myopia is described. The scanning beam of the ultrashort pulsed laser using a wavelength transmissive by the cornea is localized to potential spherical surface 212 using any one of several methods. The preferred embodiment uses contact with the cornea to identify the anterior surface of the cornea. The focus of the laser, using computer control, is then known at any time, depending on the displacement of the spot from the initial reference point. Or, the potential surface 212, at a desired depth from the anterior surface can be found at any point using the corneal profile or topography and the desired depth 214. Using such a system, the computer program directs the laser beam spot to be scanned through the corneal tissue in the same patterns and for the same purposes as described above for the contact lens 78 type of delivery system. Once a start point has been established at a desired depth, ablation commences. Any ablation path for the scanning spot can be used, such as spiral, concentric circles, adjacent linear ablations, etc. Ablation proceeds from posterior to anterior within the cornea to avoid absorption of the beam energy by plasma. Thus, the beam spot is always moving into unablated tissue.

In one embodiment (as described in FIG. 15D), the cornea is applanated by a hard material, which may be flat or curved, with a radius of curvature somewhat greater than that of the cornea. This prevents the expanding plasma and fluid resulting from ablation from distorting and displacing the cornea anteriorly, which would make the actual relation of the location of the laser spot to the desired location in the tissue unknown, as the corneal tissue is constantly being distorted by expanding plasma bubbles formed by the ablation. Contact or applanation of the anterior cornea prevents this, as the anterior cornea cannot be displaced outwardly because of the rigid applanating plate or contact lens. Ablation proceeds until the volumetric shape desired 210 has been ablated. The cavity for correction of myopia is seen to be delimited by the intersection of two potential spherical surfaces of different radii. The central width of the cavity is the difference in sagitta between these two curves with optic zone diameter D9 (typically 3–6 mm). It can be seen that an infinite number of paired surfaces may be used to achieve the same sized cavity, with the determination of shape of one defining the second. The paired surfaces are symmetric with respect to the anterior corneal surface and are centered on the visual axis 33. It is most important that in this invention an ultrashort pulsed laser is used, as this allows for reduced energy in the laser beam to achieve breakdown. This allows the production of a well-defined cavity, with smooth boundaries, and with reduced collateral damage to the adjacent corneal tissue, especially the delicate endothelium. Accuracy in this procedure is dependent on a cavity of exact shape.

Following ablation and absorption of the breakdown products, the closure of the cavity is postulated to result in posterior displacement of the central anterior cornea. However, experience has shown that this may not be accomplished, because of the rigidity of Bowman's membrane in the anterior cornea that resists bending. It is apparent that to create a new and flatter anterior cornea, there must be lateral or radial displacement of the anterior cornea over the boundary of the ablation zone, because we now demand that a given arc length of anterior cornea assume a flatter curvature over the same diameter, which will cause wrinkling or frank failure to flatten. This has been common experience with keratomileusis in the past. Thus, to overcome this problem and allow the cavitation procedure to work, the invention provides a relaxation incision 220, which can be performed before or after the cavity 210 is ablated. The purpose is to free and isolate the anterior cornea within the surgical zone from the more peripheral, thereby allowing the central portion 222 to displace itself as required, as is done in keratomileusis. This is accomplished as follows in the preferred embodiment. The laser spot 58 is scanned from the lateral edge 224 of the completed ablation zone of diameter D9 more peripherally to create a new annular surface with a radius similar to that of the anterior cornea until diameter D10 is reached. Thus, in FIG. 15S, we see ablation zone edge 224, surrounded by a plane of annular shape 226 with width 228. Upon reaching diameter D10, the spot is then scanned outward along path 230, until it exits the corneal surface. What has now been produced is a freely isolated corneal lamellar disc, free to assume a new shape without any impediment, since all attachment has been severed. This is very similar to a typical keratomileusis end result, but without the complications associated with mechanical removal of the disc and exposure of the internal cornea to infection, epithelium, etc. The actual shape of path 230 can assume any desired shape, and only one has been described. The purpose for moving peripherally to D10 rather than scanning the spot directly toward the surface at radius D9/2 is to prevent optical symptoms, which can result when the anterior cornea is incised at too small a distance from the visual axis. However, D10 may equal D9 if desired.

An alternative relaxation incision is made as follows. Rather than join the ablation cavity directly to the penetration at the surface via path 230, it may be efficacious to simply delimit the central anterior cornea with a circular incision at some desired diameter equal to or beyond D9. Thus, the scanning would produce an ablation along path 226, to some desired depth into the cornea, but made from posterior to anterior. This may allow the central cornea, in some cases, enough freedom to equilibrate without actually separating completely the lamellar disc. This may prevent gross undesired movement or frank loss of the central portion, and eliminate the need for any sutures.

FIGS. 15T–X demonstrate the use of an ultrashort pulsed laser for making various incisional patterns. Such incisions have various uses, such as for performing radial, transverse, or arcuate keratectomy for the correction of myopia and astigmatism. If used in a circumferential pattern, they can be used to cut through or trephine the cornea (laser trephine) for corneal transplantation. In all the incisional patterns to be described, an ultrashort pulsed laser operating in the transmissive part of the electromagnetic spectrum with respect to the cornea is employed.

Figure 15T:
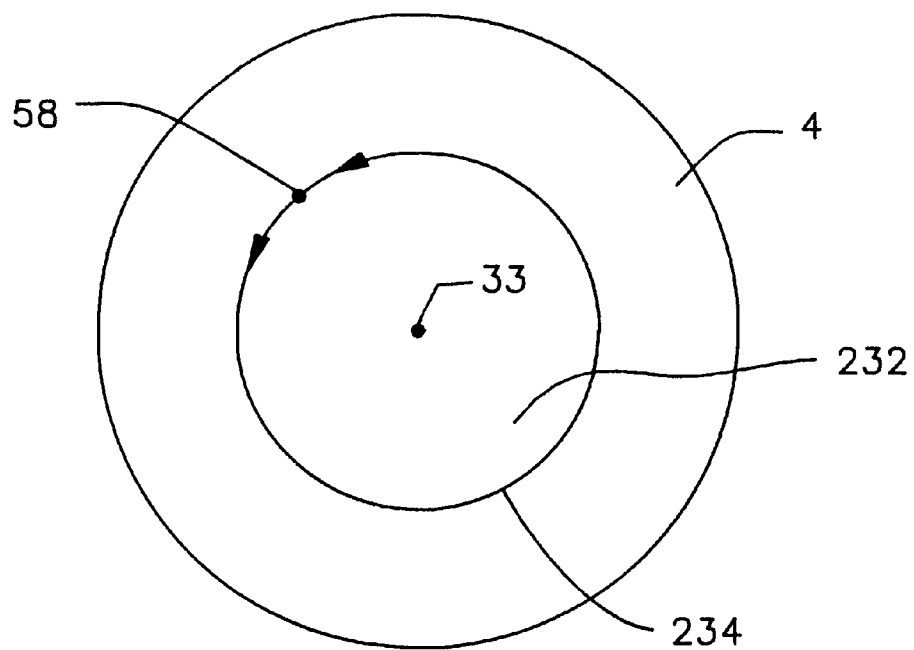
FIG. 15T is a front view of a round penetrating keratoplasty incision.

FIG. 15T demonstrates the use of the laser in corneal transplantation (penetrating keratoplasty). The object is to allow the surgeon the ability of cutting precisely a partial diameter, full thickness corneal button 232 to transplant from the donor to the host, or recipient. Typically, the walls 234 of the incision are vertical, or parallel to the visual axis 33. This provides a button whose walls are a portion of a cylinder. Also, the transplant button is typically round, as this facilitates use of mechanical trephines. In this invention, we provide for a transplant button and host opening of any shape with walls at any angle.

Figure 15U:
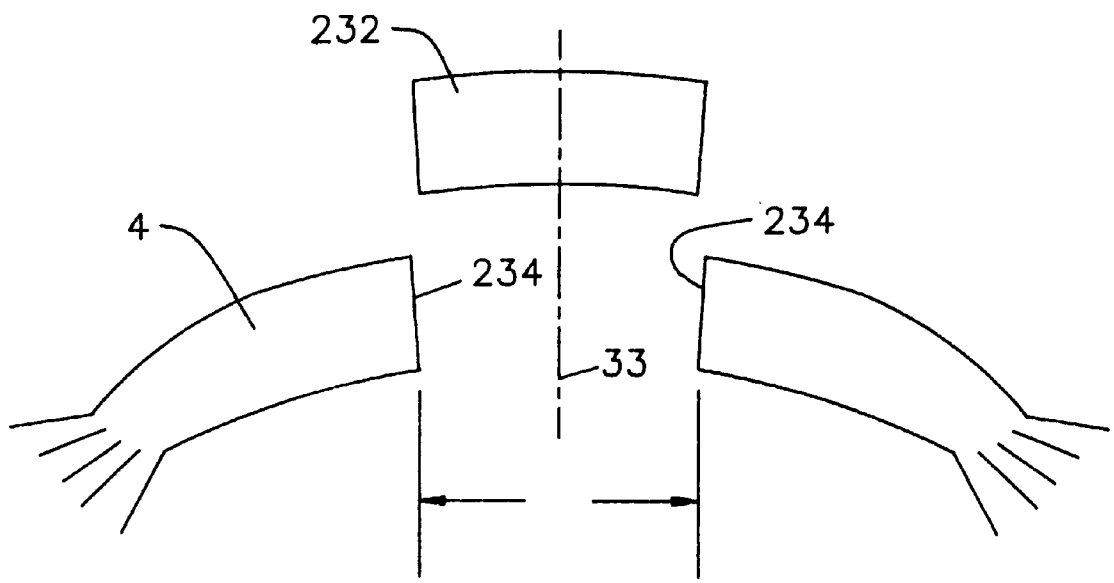
FIG. 15U is an elevation in section of the cornea demonstrating a full-thickness penetrating keratoplasty incision.

In FIG. 15U an elevation in section of the cornea is shown along with a central corneal button having been removed by the laser. The typical cornea 4 is 12–13 mm in diameter, and the typical button removed 232 is 7–9 mm in diameter. In this case the walls of the button and bed are vertical or cylindrical. The trephination is usually centered on the visual axis 33. FIG. 15T is a front view of FIG. 15U and demonstrates the circularity of the margin 234 of the button 232 removed from the peripheral cornea 4.

Figure 15V:
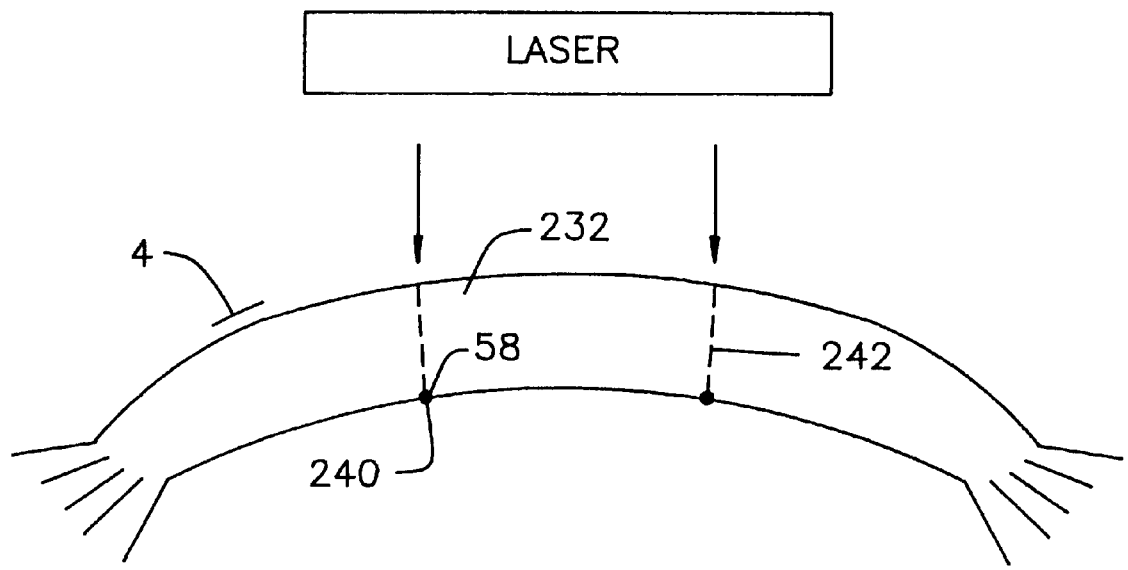
FIG. 15V is an elevation in section demonstrating the production of a penetrating keratoplasty incision by laser.

FIG. 15V demonstrates the operation of the laser in penetrating keratoplasty. The means of delivering the laser beam to the cornea have been described above. The laser beam spot of selected desired diameter is first focussed just posterior or just within the cornea 4, as desired by the given surgeon. Here it is shown just at the posterior margin 240 of the cornea. Then, the energy is delivered while scanning the laser spot such that the dotted path 242 through the cornea 4 is traversed, thereby producing a complete circular incision through the depth of the cornea. In FIG. 15T it is seen that the beam spot 58 is scanned in a circular pattern 234. Following transection of the anterior cornea, the button 232 is easily removed by the surgeon. Both the donor button and the recipient host opening are cut in the same fashion, though the diameter of the donor button is typically greater than the host opening.

Under computer control, as previously described, the wall 234 of the incision can take any shape. The delivery system simply scans such that any wall pattern is created, such as conical, and at any desired angle. Also, the shape in frontal projection can be made to vary from circular. For example, an elliptical opening can be created. Also, to correct astigmatism, the shape of the donor button and host opening can be different. For example, one may be circular and the other elliptical. Or, both can be elliptical but with different major and minor radii. When inserting a donor elliptical shape into a host opening of circular shape, for example, astigmatism or toricity of the anterior corneal surface will be induced. If the patient already had astigmatism, this operation would correct it.

Figure 15W:
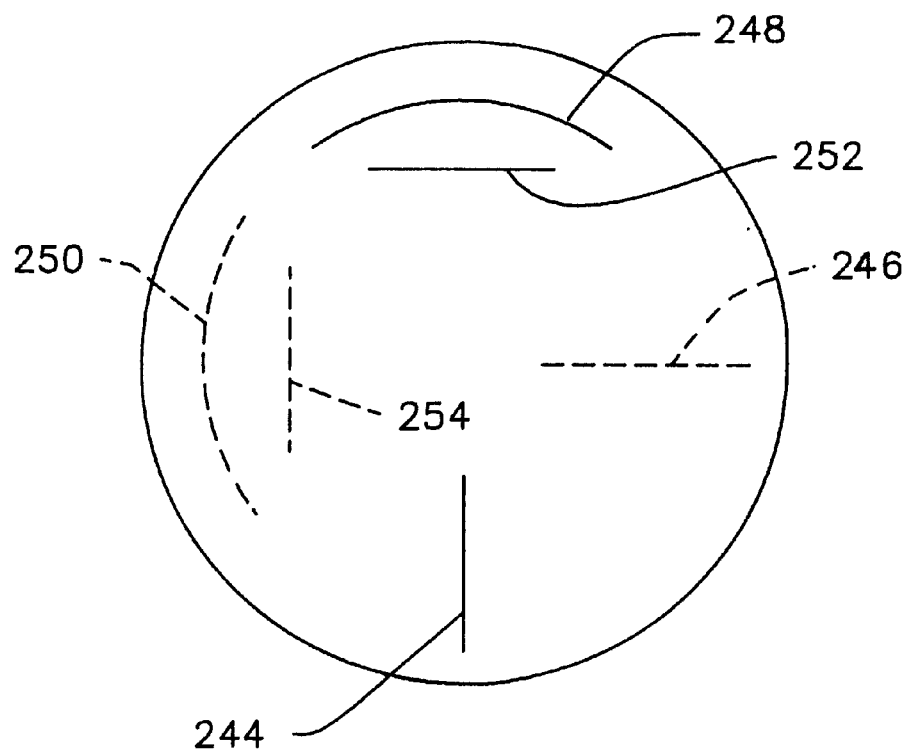
FIG. 15W is a frontal view of the cornea demonstrating various incisional patterns, some of which penetrate the anterior corneal surface (solid) and some of which do not (dotted).

FIG. 15W is used to demonstrate the use of the laser in making various incisions or excisions for correcting refractive errors such as myopia and astigmatism. In this discussion, only several commonly used patterns are described, and it is obvious that any kind of incision may be made, other than the examples given. Incisions may be made as a penetrating incision, in which case the incision begins deep in the cornea and exits by penetrating the anterior corneal surface (solid lines), or they can be made totally intrastromally or within the cornea (dashed lines), in which case they do not penetrate the anterior cornea. Incisions depicted are penetrating 244 and intrastromal 246 radial incisions for correction of myopia, penetrating 248 and intrastromal 250 arcuate incisions and penetrating 252 and intrastromal 254 transverse incisions for the correction of astigmatism. Often, incisions for correcting myopia are combined with incisions for correcting astigmatism.

Figure 15X:
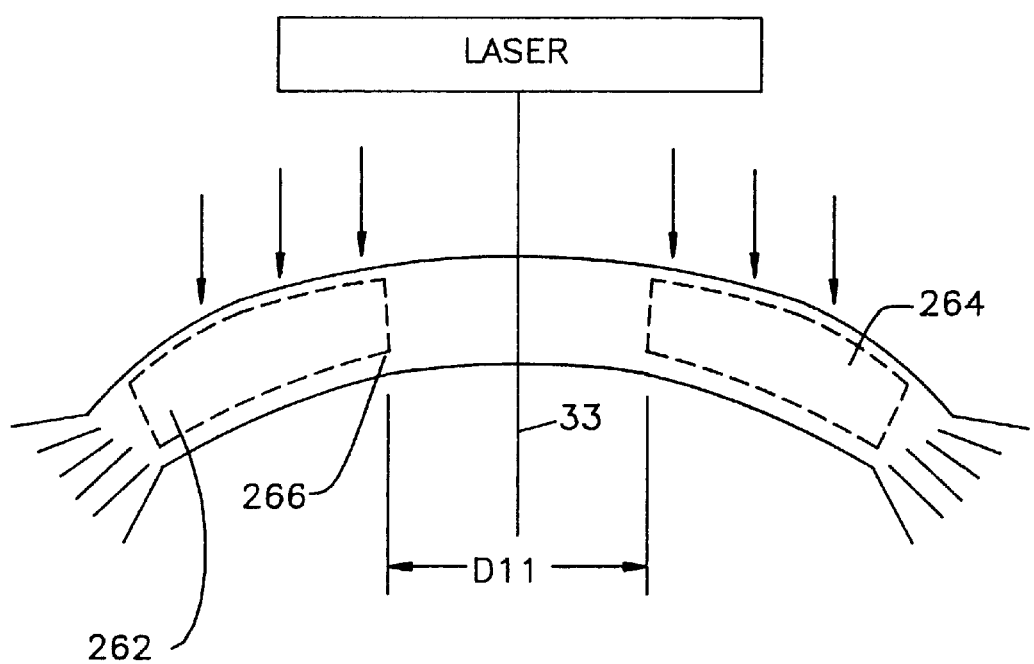
FIG. 15X is a side view of the cornea demonstrating both anterior penetrating and intrastromal radial incisions made with laser radiation.

FIG. 15X demonstrates, in an elevation in section of the cornea, radial intrastromal 262 and penetrating 264 incisions. In incisional techniques, the ablations are typically some distance from the visual axis 33 to prevent subjective visual symptoms, and often more than one is made in a symmetric fashion. The distance between the central most extents of the incisions is called the optic zone, here shown as D11. Incision 262 can be seen to be totally localized within the cornea, whereas incision 264 is seen to penetrate anteriorly. It is seen that the incisions are made deeply in the cornea, but not to its posterior surface, which is to be avoided in these techniques. Thus a layer of cornea 266 is left without incision at the end of surgery. The surgeon may select the percentage depth of the incision, and thus calculate from the corneal thickness the depth of cut and thickness of the zone uncut. The surgeon also selects the pattern or shape of the incision, its lateral extent and the diameter D11 of the zone not operated within centrally. Following the programming of all these variables into the computer, the laser delivery system is activated. The laser beam spot is located to a desired start point within the cornea, as previously described, and each incision is sequentially executed by the laser while scanning the spot under computer control. The delivery system scans from posterior to anterior along the length of the incision until the thickness of the incision is completed, whether partial thickness or penetrating, in which case the spot is scanned out through the surface to ensure penetration.

Figure 15Y:
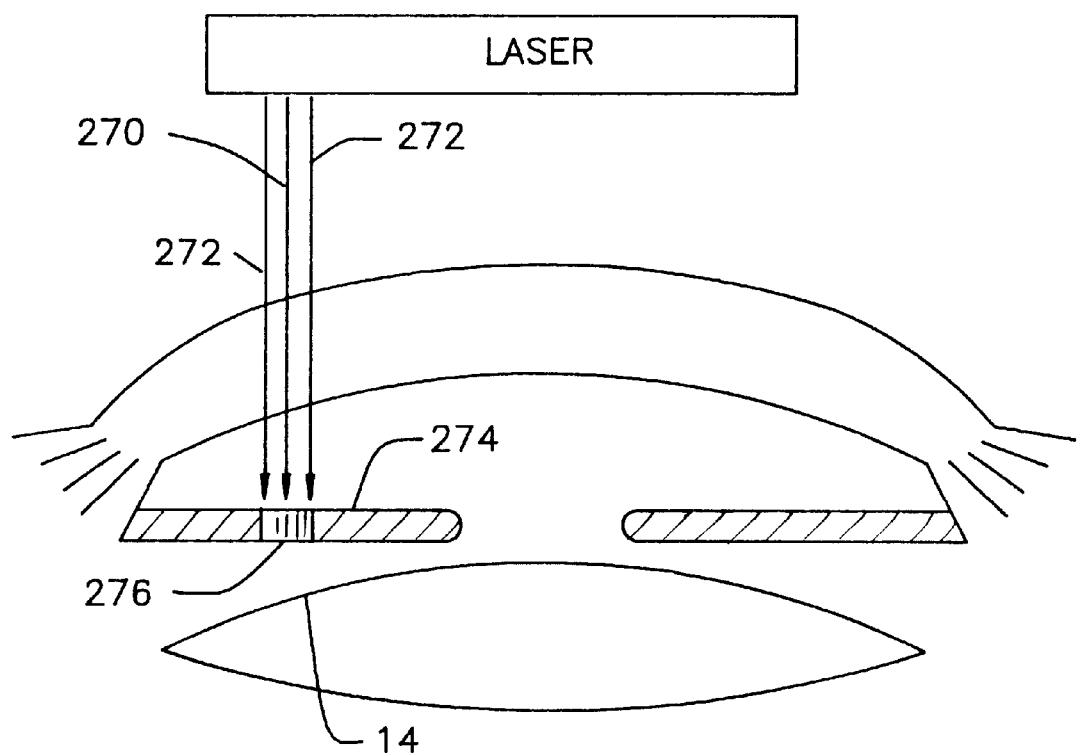
FIG. 15Y demonstrates laser iridotomy.

FIG. 15Y describes the procedure of iridotomy using the invention. Either type of delivery system previously described, contact lens or tracking system, may be used. However, the preferred embodiment is as a slit-lamp delivery system. Here, the surgeon uses a joystick to control the beam spot. The energy level, spot size, delivery pattern, and ablation time are all controlled by the surgeon. The laser has a HeNe focusing beam 270 coaxial with the ablating beam 272, and the surgeon focuses the beams at the surface of the iris 274 of the eye. Ablation begins under the control of the surgeon and the computerized beam delivery system ablated a circular area of iris. Ablation in this case is carried out from anterior to posterior, as the iris is not transparent to the laser radiation. The laser beam spot is scanned posteriorly until a through and through perforation 276 has occurred. In another embodiment, the ablation, which proceeds from the anterior surface of the iris, can be controlled to prevent accidental exposure of the anterior lens capsule 14 just behind the iris, by locking in the point of the anterior surface with respect to translation and having the computer ensure that ablation can only proceed a safe distance into the eye.

Figure 15Z:
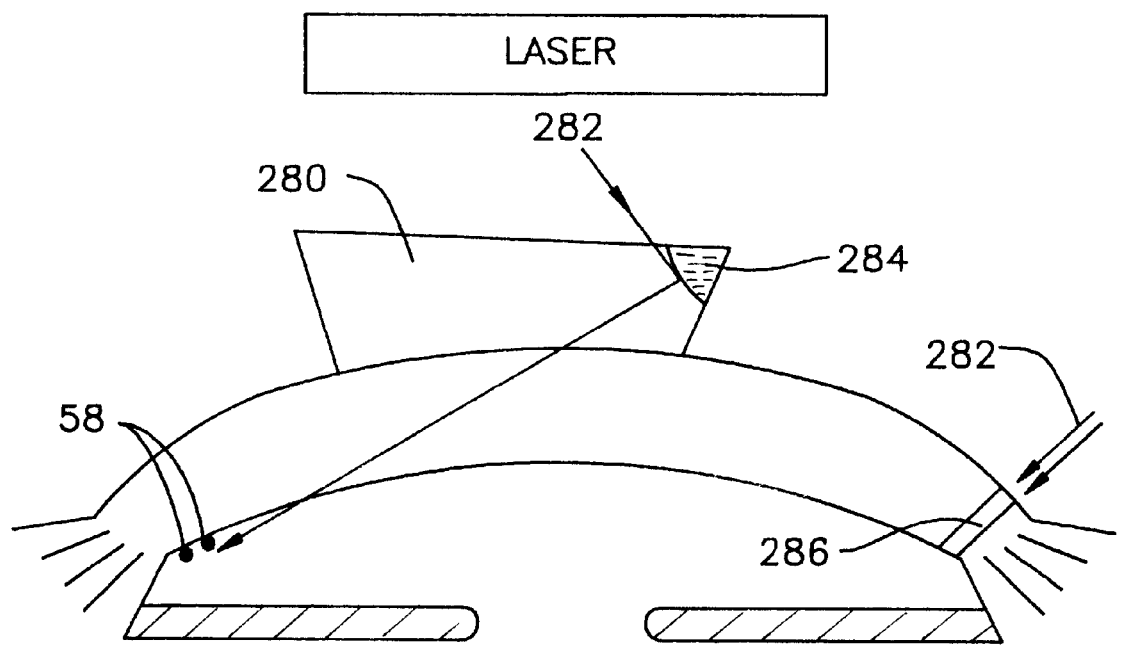
FIG. 15Z demonstrates the use of the laser for making incisions for glaucoma surgery and trabeculoplasty.

FIG. 15Z demonstrates the use of the laser for glaucoma filtration surgery. Here the procedures of trabeculoplasty, trabeculectomy and sclerostomy are described. To perform laser trabeculoplasty, a slit lamp delivery system is the preferred embodiment. The surgeon places a Goldmann contact lens 280 on the eye, which is standard practice, and fires the laser beam 282 onto a mirror 284 in the Goldmann lens 280 such that the laser spot 58 ablates a small spot of trabecular tissue, thereby deforming its contour and aiding in fluid outflow. The spot size, energy level, depth of ablation, etc., are all controlled by the surgeon.

FIG. 15Z also shows other filtering procedures to reduce intraocular pressure. A drainage channel 286 can be bored into the eye by laser radiation 288 at the limbal area, reaching deeply into the eye's wall until fluid seeps out or until penetration. Alternatively, the drainage channel can be partial thickness and covered by a flap of the eye's wall externally for safety. These procedures are well known and not described in detail. Lastly, the drainage channel can be made using the Goldmann lens, in which case it can be initiated inside the eye and carried outward for partial or complete penetration. In all glaucoma procedures, the HeNe focussing beam, etc. is used, but details are not shown as it has been described before.

FIGS. 15A1–B1 demonstrate the performance of anterior capsulectomy (capsulorhexis) and posterior capsulectomy of the lens 289. In FIG. 15A1, the left side demonstrates half an anterior capsule 290 opened by the invention, whereas the right side a capsulectomy 292 performed manually or with previous laser technology, should it be used for this application. This is accomplished with an ultrashort pulsed laser using a wavelength transmitted by the cornea. The purpose is to allow the surgeon to open the lens capsule with a smoothly contoured incision of desired shape and with minimal trauma to facilitate the cataract surgery to follow, or to allow an unimpeded path for light from the environment to the retina in post-cataract patients with an opacified posterior capsule. The ability to open a lens capsule in a regular and controlled manner is of great importance. A smooth and regular opening in the anterior capsule prevents the complications of capsule tear or rupture, or difficulties in inserting the intraocular lens because of an inappropriately sized opening. Also, opening either capsule with the invention significantly reduces the acoustic shock waves within the eye and reduces the possibilities of retinal complications or damage to the prosthetic lens.

The operation is performed as follows. The focus of the laser beam spot is localized to the anterior lens capsule by direct visualization using a visual HeNe laser beam focussed to the same focal point as the ablating laser, as typically done, at distance D11/2 from the center of the anterior lens capsule 294. This defines the diameter of the capsulorhexis. Then, the surgeon displaces the HeNe positioning beam just posteriorly to the capsule at D11/2, or a selected distance can be programmed into the beam control computer, and photodisruption begins. The beam 296 is directed in a circular pattern, beginning posteriorly and translating anteriorly while following path 298, to ensure complete transection of the capsule. The cutting process can be totally computerized once the reference point on the capsule has been fixed, or the surgeon can terminate the process when the capsule has been visibly cut for 360 degrees. Typically, the surgeon will manually remove the freed central layer of capsule within the ablation boundary shortly thereafter, during cataract surgery.

For a posterior capsulectomy, the process is similar, except that D11 is significantly less, typically 1–3 mm. A posterior capsulectomy is performed to open an opacified posterior lens capsule in patients who have undergone cataract surgery, and whose opacified posterior capsule impedes the passage of light rays to the retina, decreasing vision. Also, the process of removing the posterior capsule is carried out without anticipation of entering the eye. Thus, to remove the capsule central to the 360 degree circular ablation, the computer may direct a series of concentric circular ablations, or any other pattern to totally destroy the central area within the circular area of diameter D11, thus providing an unimpeded path for light from the environment to the retina.

FIGS. 15C1–D1 demonstrate the principle of phacorefractive ablation. The purpose of this procedure is to modify the refractive power of the eye by altering the curvature, and hence refractive power, of the lens as opposed to modification of corneal refractive power by altering corneal curvature. Altering the shape of the cornea to produce refractive change is known to be accompanied by various subjective symptoms. It is established that a given degree of irregularity or abnormality in a refractive surface causes more symptoms if it is located further from the focal point of the eye. It has been established that such aberrations would be reduced if located at the position of the lens. Also, the capsule of the lens is pliable and will easily deform itself around the cortical lens substance with new curvature. The concept is to ablate some of the substance of the lens 299 of the eye in a non-traumatic fashion such that lens material is removed from under the anterior lens capsule 14 in a controlled fashion. The laser source is an ultrashort, pulsed laser, using a wavelength transmissive to the cornea and the lens. The laser is focussed within the lens itself, scanned in a pattern appropriate for the shape of the calculated ablation, and, by photodisruption, the lens material is ablated. Following absorption of the breakdown products, the anterior lens capsule is displaced to close the resulting potential space within the lens. This displacement is enhanced by the pressure vector 302 exerted on the capsule by the intraocular pressure, which is approximately 10–23 mm Hg. Although complete ablation in the surgical zone is preferred, it is possible that a change in the viscoelastic nature of the lens material may also allow for a surgically satisfactory result, although perhaps of lesser magnitude. It is most important that the anterior lens capsule 14 not be damaged in the process. Thus, the positioning and localization of the laser beam spot is critical. For this reason a safety zone of width 304 is thus left posterior to the anterior lens capsule 14. The laser beam may be localized with respect to the anterior lens capsule by using a HeNe laser that is arranged such that the focal point is identical to the ablating laser. The HeNe beam can be focused on the anterior lens capsule 14 and the zero position noted by the computer. Then the safety distance 304 is added to localize the laser focal spot posterior to the anterior lens capsule 14. Alternatively, since the distances between optical components of the eye can be known accurately by using ultrasound measurement, the laser beam can first be oriented to the front of the cornea by the contact lens delivery system. Then, the measured distance of the anterior lens capsule from the anterior corneal surface is programmed in along with the width of safety zone 306 before beginning the ablation. Ablation begins posteriorly and the laser spot is scanned in any of several patterns as previously described until the entire volume 299 has been ablated, thus terminating at the calculated safety distance. Ablation proceeds from posterior to anterior to avoid absorption of the beam energy by the plasma already formed. Initially, plasma or fluid is produced. The diameter D12 of the ablation zone may be in the range of 3–7 mm, but not limited to this range. In addition, astigmatism, with or without myopia, can also be corrected by ablating a cylindric or toric pattern rather than a spherical one, as previously described. Also, hyperopia, with or without astigmatism is also correctable. In this case, the shape of the volume ablated is such that width 304 is minimal at the point where the visual axis intersects the lens and the ablation width increases as one moves radially from the center, or visual axis. Any pattern, aspheric or spheric, can be programmed into the computer to control the ablation geometry for a desired result.

FIG. 15E1 demonstrates the use of the laser to cut vitreous bands or membranes. A vitreous membrane 20 is shown lying close to the retina. The preferred embodiment is the slit-lamp delivery system with HeNe focussing laser as previously described. The surgeon focuses the beam directly on the membrane, using the Goldmann type lens 280. With a foot or manual control, the beam 88 transmissive by the cornea, lens and vitreous, is applied to the membrane, and the surgeon uses a joy stick control to manually guide the beam through the membrane to achieve the desired cutting or ablation effect. The surgeon controls the energy, spot size, and laser beam burst time. The gentle femptosecond pulse width laser reduces acoustic shock and allows the surgeon to operate closer to the retina than with current technology.

What is claimed is:

1. A method for performing a lamellar keratectomy on tissue of a cornea, whereby a partial thickness lamellar disc of tissue is freed from surrounding corneal tissue, said method comprising the steps of:

generating a pulsed laser beam by a pulsed laser apparatus, said beam having pulses having a duration in a range of about 10 femptoseconds to about 2 picoseconds;

said pulses having an energy density at a point of interaction in a material of less than $5\ \mu J/(10\ \mu m)^2$;

said pulses having a wavelength transmissive in eye tissue;

Wherein the wavelength is in one of a group of ranges consisting of about 400 nm to about 1900 nm, about 2.1 $\mu$m to about 2.8 $\mu$m, and longer than about 3.1 $\mu$m;

said beam having up to approximately 100,000 pulses per second;

wherein a lasing medium of the pulsed laser apparatus is a broad gain bandwidth laser;

wherein the lasing medium of the pulsed laser apparatus uses lasing ions such as titanium, chromium or neodymium (for example, $Ti_3:Al_2O_3$, $Cr:LiSrAlF_6$, Nd:YLF, or similar lasers);

focusing the laser pulses at a selected interaction point in the material;

wherein the selected interaction point has a diameter in a range of about 1 $\mu$m to about 30 $\mu$m;

positioning the laser pulses within a selected portion of the material;

determining a position of the laser pulses within the material;

controlling the diameter of the laser pulses;

determining the diameter of the laser pulses;

controlling the intensity of the laser pulses;

determining the intensity of the laser pulses;
controllably blocking the laser pulses from the material;
directing the laser beam to a selected start position within the cornea;
scanning a laser spot through the corneal tissue in a predetermined manner such that the lamellar disc of the tissue to be removed is outlined and freed from the surrounding corneal tissue by ablating scanned tissue along a path scanned;

whereby an edge shape of the partial thickness lamellar disc is varied as desired for specific applications by altering the path of the scanning spot as it traverses from within the cornea to finally exit the cornea anteriorly.

2. A method according to claim 1 wherein the pulses of the laser beam are in the range of 10–400 fs.

3. A method according to claim 1, wherein the laser apparatus comprises a seed laser and a scanner-amplifier laser.

4. A method according to claim 3, in which the lasing ion in the solid state laser crystal of the scanner-amplifier is titanium ($Ti_3:Al_2O_3$, for example).

5. A method according to claim 1 in which controlling the diameter of the laser pulses comprises reflecting part of the laser beam by a beam-splitting mirror to a beam diameter sensor comprising a high sensitivity, low contrast imaging device.

6. A method according to claim 1, in which the intensity of the laser pulses is determined by partially reflecting the laser beam with a partially transmissive beam-splitting mirror to a beam intensity sensor.

7. A method for performing a photorefractive lamellar keratectomy on corneal tissue, comprising the steps of:
removing a partial thickness lamellar disc of tissue intact from an anterior cornea, such lamellar disc being of varying thickness such that said lamellar disc is a lamellar lens with refractive power, the removing of which leaves behind a remaining cornea having a new anterior corneal surface of refractive power different than prior to the keratectomy;
said method comprising the further steps of:
generating a pulsed laser beam, having a duration of ultrashort pulse width, and having an electromagnetic frequency that is transmitted by the cornea;
directing the laser beam to a selected start position within the cornea;
selecting a power density for said laser beam;
scanning a laser spot through the corneal tissue in a predetermined manner such that said laser spot outlines and isolates the disc to be removed from the remaining cornea by ablating tissue along a path scanned.

8. A method according to claim 7 where the resected lamellar lens is a convex lens for correction of myopia.

9. A method according to claim 7 in which the resected lammellar lens is concave for correction of hyperopia.

10. A method according to claim 7 where the resected lens is aspheric in the sense that there is a peripheral zone of varying curvature, comprising a means for improving wound healing and surgical result.

11. A method according to claim 7 in which the resected lamellar lens is an aspheric lens for correction of astigmatism, regular and irregular, and spherical aberration.

12. A method according to claim 7 wherein the pulse width of the laser beam is in the range of 10–400 fs.

13. A method according to claim 7 whereby an edge shape of the resected lamellar disc may be varied as desired for specific applications by altering the path of the scanned spot as it traverses from within the cornea to finally exit the cornea anteriorly.

14. A method for performing a lamellar keratectomy on tissue of a cornea, whereby a partial thickness lamellar disc of tissue is freed from surrounding corneal tissue, said method comprising the steps of:
generating a pulsed laser beam by a pulsed laser apparatus, said beam having pulses having a duration in a range of about 10 femtoseconds to about 2 picoseconds;
said pulses having an energy density at a point of interaction in a material of less than $5\ \mu J/(10\ \mu m)^2$;
said pulses having a wavelength transmissive in eye tissue;
wherein the wavelength is in one of a group of ranges consisting of about 400 nm to about 1900 nm, about $2.1\mu$ to about $2.8\mu$, and longer than about $3.1\ \mu$;
said beam having up to approximately 100,000 pulses per second;
wherein a lasing medium of the pulsed laser apparatus is a broad gain bandwidth laser;
wherein the lasing medium of the pulsed laser apparatus uses lasing ions such as titanium, chromium or neodymium (for example, $Ti_3:Al_2O_3$, $Cr:LiSrAlF_6$, $Nd:YLF$, or similar lasers);
focusing the laser pulses at a selected interaction point in the material;
wherein the selected interaction point has a diameter in a range of about $1\ \mu m$ to about $30\ \mu m$;
positioning the laser pulses within a selected portion of the material;
determining a position of the laser pulses within the material;
controlling the diameter of the laser pulses;
determining the diameter of the laser pulses;
controlling the intensity of the laser pulses;
determining the intensity of the laser pulses;
controllably blocking the laser pulses from the material;
directing the laser beam to a selected start position within the cornea;
scanning a laser spot through the corneal tissue in a predetermined manner such that the lamellar disc of tissue to be removed in outlined and freed from the surrounding corneal tissue by ablating scanned tissue along a path scanned;
whereby an edge shape of the resected lamellar disc is varied as desired for specific applications by altering the path of the scanning spot as said scanning spot traverses from within the cornea to finally exit the cornea anteriorly;
the lamellar disc being of varying thickness such that the lamellar disc is a lens with refractive power, the removal of which lens leaves behind a new anterior corneal surface of refractive power different than prior to the keratectomy where the resected lens is aspheric in the sense that there is a peripheral zone of varying curvature, comprising a means for improving wound healing and surgical result;
wherein the pulse width of the laser beam is in the range of 10–400 fs;
whereby an edge shape of the resected lamellar disc may be varied as desired for specific applications by altering the path of the scanned spot as the scanned spot traverses from within the cornea to finally exit the cornea anteriorly;
wherein the pulsed laser apparatus comprises a seed laser and a scanner-amplifier laser;

in which the lasing ion in the solid state laser crystal of the scanner-amplifier is titanium ($Ti_3:Al_2O_3$, for example);

in which controlling the diameter of the laser pulses comprises reflecting part of the laser beam by a beam-splitting mirror to a beam diameter sensor comprising a high sensitivity, low contrast imaging device; and in which the intensity of the laser pulses is determined by partially reflecting the laser beam with a partially transmissive beam-splitting mirror to a beam intensity sensor.

* * * * *